US008853177B2

(12) United States Patent
Zhu et al.

(10) Patent No.: US 8,853,177 B2
(45) Date of Patent: Oct. 7, 2014

(54) USE OF INHIBITORS OF TOLL-LIKE RECEPTORS IN THE PREVENTION AND TREATMENT OF HYPERCHOLESTEROLEMIA AND HYPERLIPIDEMIA AND DISEASES RELATED THERETO

(75) Inventors: Fu-Gang Zhu, Bedford, MA (US); Ekambar Kandimalla, Southboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 648 days.

(21) Appl. No.: 12/574,576

(22) Filed: Oct. 6, 2009

(65) Prior Publication Data

US 2010/0098685 A1    Apr. 22, 2010

Related U.S. Application Data

(60) Provisional application No. 61/102,974, filed on Oct. 6, 2008.

(51) Int. Cl.
*A61K 48/00* (2006.01)
*C07H 21/02* (2006.01)
*C07H 21/04* (2006.01)

(52) U.S. Cl.
USPC ............................. 514/44; 536/23.1; 536/24.5

(58) Field of Classification Search
None
See application file for complete search history.

(56) References Cited

U.S. PATENT DOCUMENTS

| | | | |
|---|---|---|---|
| 6,426,334 B1 | 7/2002 | Agrawal et al. | |
| 6,476,000 B1 | 11/2002 | Agrawal | |
| 6,815,429 B2 | 11/2004 | Agrawal | |
| 7,105,495 B2 | 9/2006 | Agrawal | |
| 8,357,665 B2 | 1/2013 | Kandimalla et al. | |
| 8,377,898 B2 | 2/2013 | Kandimalla et al. | |
| 8,383,598 B2 | 2/2013 | Kandimalla et al. | |
| 8,399,423 B2 | 3/2013 | Kandimalla et al. | |
| 8,426,375 B2 | 4/2013 | Kandimalla et al. | |
| 2003/0059482 A1 | 3/2003 | Siskind | |
| 2004/0009949 A1 | 1/2004 | Krieg | |
| 2004/0097719 A1 | 5/2004 | Agrawal et al. | |
| 2005/0059616 A1 | 3/2005 | Kelly et al. | |
| 2005/0239733 A1 | 10/2005 | Jurk et al. | |
| 2006/0074040 A1 | 4/2006 | Kandimalla et al. | |
| 2006/0193869 A1 | 8/2006 | Barrat et al. | |
| 2007/0238678 A1 | 10/2007 | Barrat et al. | |
| 2009/0053148 A1 | 2/2009 | Kandimalla et al. | |
| 2009/0131512 A1 | 5/2009 | Barrat et al. | |
| 2011/0003885 A1 | 1/2011 | Barrat et al. | |
| 2011/0214194 A1* | 9/2011 | Beutler et al. | 800/18 |

FOREIGN PATENT DOCUMENTS

| | | |
|---|---|---|
| EP | 1393745 A1 | 3/2004 |
| WO | 01/83503 A2 | 11/2001 |
| WO | 03/103708 A1 | 2/2003 |
| WO | 03/103586 | 12/2003 |
| WO | 2004/094671 A2 | 11/2004 |
| WO | 2005/007672 A2 | 1/2005 |
| WO | 2005-058349 | 6/2005 |
| WO | 2006-063072 | 6/2006 |
| WO | 2007/038720 A2 | 4/2007 |

OTHER PUBLICATIONS

Lenert et al., "Inhibitory Oligonucleotides Block the Induction of AP-1 Transcription Factor by Stimulatory CpG Oligonucleotides in B Cells"; Antisense & Nucleic Acid Drug Development; 13(3):143-150 (2003).
Gursel et al., "Repetitive Elements in Mammalian Telomeres Suppress Bacterial DNA-Induced Immune Activation"; The Journal of Immunology, 171:1393-1400 (2003).
Shirota et al., "Suppressive Oligodeoxynucleotides Protect Mice From Lethal Endotoxic Shock", The Journal of Immunology, 174:4579-4583 (2005).
Shirota et al., "Suppressive Oligodeoxynucleotides Inhibit Th1 Differentiation by Blocking Ifn-y-and IL-12 Mediated Signaling", The Journal of Immunology, 173:5002-5007 (2004).
Yamada et al., "Effect of Suppressive DNA on CpG-Induced Immune Activation", The Journal of Immunology, 169:5590-5594 (2002).
Zeuner et al., "Influence of Stimulatory and Suppressive DNA Motifs on Host Susceptibility to Inflammatory Arthritis", Arthritis & Rheumatism, 48(6):1701-1707 (2003).
Klinman et al., "Regulation of CpG-Induced Immune Activation by Suppressive Oligodeoxynucleotides", Ann. N.Y. Acad. Sci., 1002:112-123 (2003).
Duramad et al.; "Inhibitors of TLR-9 Act on Multiple Cell Subsets in Mouse and Man in Vitro and Prevent Death in Vivo from Systemic Inflammation", The Journal of Immunology, 174:5193-5200 (2005).
Hornung et al., "Quantitative Expression of Toll-Like Receptor 1-10 mRNA in Cellular Subsets of Human Peripheral Blood Mononuclear Cells and Sensitivity to CpG Oligodeoxynucleotides", J. Immunol.,168:4531-4537(2002).
Poltorak et al., "Defective LPS Signaling in C3H/Hej and C57BL/1 OScCr Mice: Mutations in T1r4 Gene", Science, 282:2085-2088 (1998).

(Continued)

*Primary Examiner* — Amy Bowman
(74) *Attorney, Agent, or Firm* — Wood, Phillips, Katz, Clark & Mortimer

(57) ABSTRACT

The invention provides the use of TLR inhibitors or a pharmaceutically acceptable derivative thereof, optionally in combination with one or more lipid lowering composition, cholesterol lowering composition, diuretics, non-steroidal anti-inflammatory compounds (NSAIDs), antibodies, antisense oligonucleotides, TLR agonists, TLR antagonists, peptides, proteins or gene therapy vectors or combinations thereof for the prevention or treatment of hypercholesterolemia and/or hyperlipidemia and/or diseases associated therewith.

42 Claims, 8 Drawing Sheets

(56) References Cited

OTHER PUBLICATIONS

Underhill et al., "The Toll-like Receptor 2 is Recruited to Macrophage Phagosomes and Discriminates Between Pathogens", Nature, 401:811-815 (1999).
Hayashi et al., "The Innate Immune Response to Bacterial Flagellin is Mediated by Toll-like Receptor 5", Nature, 410:1099-1103 (2001).
Zhang et al., "A Toll-like Receptor that Prevents Infection by Uropathogenic Bacteria", Science, 303:1522-1525 (2004).
Meier et al., Cell. "Toll-like Receptor (TLR) 2 and TLR4 are Essential for Aspergillus-Induced Activation of Murine Macrophages", Cellular Microbiol., 5(8):561-570 (2003).
Campos et al., "Activation of Toll-like Receptor-2 by Glycosyiphosphatidylinositol Anchors from Protozoan Parasite", J. Immunol., 167:416-423 (2001).
Hoebe et al., "Identification of Lps2 as a Key Transducer of MyD88-independent TIR Signaling", Nature, 424:743-748 (2003).
Lund et al., "Toll-like Receptor 9-Mediated Recognition of Herpes Simplex Virus-2 by Plasmacytoid Dendritic Cells", J. Exp. Med., 198(3):513-520 (2003).
Heil et al., "Species-Specific Recognition of Single-Stranded; RNA via Toll-like Receptor 7 and 8", Science, 303:1526-1529 (2004).
Diebold et al., "Innate Antiviral Responses by Means of TLR7-Mediated Recognition of Single-Stranded RNA" Science 303:1529-1531 (2004).
Hornung et al., "Replication-Dependent Potent IFN-a Induction in Human Plasmacytoid Dendritic Cells by a Single-Stranded RNA Virus", J. Immunol. 173:5935-5943 (2004).
Akira et al., "Toll-like Receptors: Critical Proteins Linking Innate and Acquired Immunity", Nature Immunol., 2 (8):675-680 (2001).
Medzhitov, R., "Toll-like Receptors and Innate immunity", Nature Rev. Immunol 1:135-145 (2001).
Cook et al., "Toll-like Receptors in the Pathogenesis of Human Disease", Nature Immunol, 5(10):975I 979 (2004).
Liew et al, "Negative Regulation, of Toll-like Receptor-Mediated Immune Responses", Nature, 5:446-458 (2005).
Hemnil et al., "Small Antiviral Compounds Activate Immune Cells via the TLR7 My88-Dependent Signaling Pathway", Nat. Immunol., 3(2):196-200-(2002).
Jurk et al., "Human TLR7 or TLR8 Independently Confer Responsiveness to the Antiviral Compound R848", Nat. Immunol. 3(6):499 (2002).
Lee et al., Molecular Basis for the Immunostimulatory Activity of Guanine Nucleoside Analogs: Activation of Toll-like Receptor 7 PNAS 100(11):6646-6651(2003).
Alexopoulou, L. et al., "Recognition of Double-Stranded RNA- and Activation of NFKB by Toll-like Receptor 3", Nature, 413:732-738 (2001).
Tokunaga et al., "Antitumor Activity by Deoxyribonucleic Acid Fraction from *Mycobactelium bovis* BCG. I. Isolation, Physicochemical Characterization, and Antitumor Activity", J. Natl. Cancer Inst., 72(4):955-962 (1984).
Shimada et al., "In Vivo Augmentation of Natural Killer Cell Activity with a Deoxyribonucleic Acid Fraction of BCG", Jpn. J. Cancer Res., 77:808-816(1986).
Yamamoto et al., "In Vitro Augmentation of Natural' Killer Cell Activity and Production of Interferon α/β and γ with Deoxyribonucleic Acid Fraction from *Mycobactenium bovis* BCG", Jpn J Cancer Res. 79:866-873 (1988).
Zhao et al., "Effect of-Different Chemically Modified Oligodeoxynucleotides on Immune Stimulation", Biochem; Pharma., 51:173-182 (1996).
Hemmi et al., "A Toll-like Receptor Recognizes Bacterial DNA", Nature, 408:740-745 (2000).
Zhao et al., "Modulation of Oligonucleotide Induced Immune Stimulation by Cyclodextrin Analogs", Biochem. Pharma., 52:1537-1544 (1996).
Zhao et al., "Pattern and Kinetics of Cytokine Production Following Administration of Phosphorothioate Oligonucleotides in Mice", Antisense Nuci. Acid Drug Dev., 7495-502 (1997).

Zhao et al., "Site of Chemical Modifications in CpG containing Phosphorothioate Oligodeoxynucleotide Modulates its Immunostimulatory Activity", BioorgMed. Chem. Lett., 9:3453-3458 (1999).
Zhao et al., "Immunostimulatory Activity of CpG Containing Phosphorothioate Oligodeoxynucleotide is Modulated by Modification of a Single Deoxynucleoside", Bioorg. Med. Chem. Lett., 10:1051-1054.
Yu et at., "Accessible 5'-End of CpG-Containing Phosphorothioate Oligodeoxynucleotides is Essential for Immunostimulatory Activity", Bioorg. Med. Chem. Left.. 10:2585-2588 (2000.
Yu et al., "Modulation of immunostimulatory Activity of CpG Pligonucleotides by Site-Specific Deletion of Nucleobases", Bioorg. Med. Chem. Lett., 11:2265-2267 (2001).
Kandimalla et al., "Effect of Chemical Modifications of Cytosine and Guaninein a CpG Motif of Oligonucleotides: Structure-Immunostimulatory Activity Relationships", Bioorg. Med. Chem., 9:807-813 (2001).
Kandimalla et al., "Immunomodulatory Oligonucleotides Containing a Cytosine-Phosphate-2'—Deoxy-7-Deazaguanosine Motif as Potent toll-like Receptor 9 Agonists", Proc Natl Acad Sci USA 102(19):6925-6930 (2005).
Kandimalla et al., "A Dinucleotide Motif in Oligonucleotides Shows Potent Immunomodulatory Activity and Overrides Species-Specific Recognition Observed with CpG Motif". Proc Natl. Acad. Sci. USA, 100(24):14303-14308 (2003).
Cong etal., "Self-Stabilized CpG DNAs Optimally Activate Human B cells and Planiacytoid Dendritic Cells", Biochem. Biophys. Res. Commun., 310:11331139 (2003).
Kandimalla et al., "Secondary Structures in CpG Oligoniicleotides Affecf Immunostimulatory Activity", Biocehm. Biophys. Res. Commun., 306:948-953 (2003).
Kandimalla et al., "Divergent Synthetic Nucleotide Motif Recognition Pattern: Design and Development of Potent Immunomodulatory Oligodeoxyribonucleotide Agents with Distinct Cytokine Induction Profiles", Nucleic: Acids Res., 31 (9):2393-2400 (2003).
Yu et al., "Requirement of Nucleobase Proximal to CpG Dinucleotide for Immunostimulatory Activity of Synthetic CpG DNA", Bioorg. Med. Chem., 11:459-464 (2003).
Bhagat et al., "CpG Penta and Hexadeoxyribonucleotides as Potent Immunomodulatory Agents", Biochem. Biophys. Res. Comm., 300:853-861 (2003).
Yu et al., "Potent CpG Oligonucleotides Containing Phbsphodiester Linkages in Vitro and in Vivo Immunostimulatory Properties", Biochem. and Biophys. Res. Comm., 297:83-90 (2002).
Yu et al., "Design Synthesis and Immunostimulatory Properties of CpG DNAs Containing Alkyl Linker Substitutions: Role of Nucleosides in the Flanking Sequences", J. Med. Chem. 45:4540-4548 (2002).
Noronha et al., "Synthesis and Biophysical Properties of Arabinonucleic Acid(ANA): Circular Dichroic Spectra, Melting Temperatures, and Ribonuclease H Susceptibility of ANA-RNA Hybrid Duplexes", Biochem., 39:7050-7062 (2000).
Yu et al., "'Immunomers' Novel 3'-3"Linked CpG Oligodeoxyribonucleotides as Potent Immunomodulatory Agents, Nucleic Acids Re., 30(20):4460-4469 (2002).
Kandimalla et al., "Conjugations of Ligands at the 5'-End of CpG DNA Affects Immunostimulatory Activity", Bioconjugate Chem., 13:966-974 (2002).
Yu et al., "Immunostimulatory Properties of Phosphorothioate CpG DNA Containing Both 3'-5'-and 2'-5'Internucleotide Linkages", Nucleic Acids Res., 30(7):1613-1619 (2002).
Kandimalla et al., "Effect of chemical Modifications of Cytosine and Guanine in a CpG-Motif of Oligonucleotides: Structure-Immunostimulatory Activity Relationships", Bioorg. Med. Chem., 9:807-813 (2001).
Yu et al., "Accessible, 5-End of CpG-Containing Phosphorothioate Oligodeoxynucleotides is Essential for Immunostimulatory Activity", Bioorg. Med. Chem., 10:2585-2588 (2000).
Putta et al., 'Novel Oligodeoxynucleotide Agonists of TLR9 Containing N3-Me-dC or N1-Me-dG Modifications, Nucleic Acids Res., 34(11):3231-3238(2006).

(56) References Cited

OTHER PUBLICATIONS

Lenert et al., "Structural Characterization of the Inhibitory DNA Motif for the TypeA (D)-CpG-induced Cytokine Secretion and NK-Cell Lytic Activity in Mouse Spleen Cells", DNA and Cell Biol., 22(10):621-631 (2003).

Chen et al., "Identification of Methylated CpG Motifs as Inhibitors of the Immune Stimulatory CpG Motifs", Gene Therapy, 8:1024-1032 (2001).

Stunz et al., "Inhibitory Oligonucleotides Specifically Block Effects of Stimulatory CpG Oligonucleotides in B Cells", Eur. J. Immunol., 32:1212-1222 (2002).

Duramad et al., "Inhibitors of TLR-9 Act on Multiple Cell Subsets in Mouse-and-Man in Vitro and Prevent Death in Vivo from Systemic Inflammation", The Journal of Immunol., 174:51935200 (2005).

Patole et al., "G-Rich DNA Suppresses Systemic Lupus", J. Am. Soc. Nephrol., 16:3273-3280 (2005).

Verthelyi et al., "Human Peripheral Blood Cells Differentially Recognize and Respond to Two Distinct CpG Motifs", The Journal of Immunol. 166:2372-2377 (2001).

Gursel et al., "Differential and Competitive Activation of Human Immune Cells by Distinct Classes of CpG Oligodeoxynucleotide", Journal of Leukocyte Biol., 71:813-820 (2002).

Krug et al., "Identification of CpG Oligonucleotide Sequences with High Induction of IFN-a/B in Plasmacytoid Dendritic Cells", Eur. J. Immunol., 31:2154-2163 (2001).

Ballas et al., "Divergent Therapeutic and Immunologic Effects of Oligodeoxynucleotides with Distinct CpG Motifs", The Journal of Immunol., 167:4878-4886 (2001).

Verthelyi et al., "CpG Oligodeoxynucleotides Protect Normal and SI V-Infected Macaques from Leishmania Infection", The Journal of Immunol., 170:4717-4723 (2003).

McShan et al., 'Inhibition of Transcription of HIV-1 in Infected Human Cells by Oligodeoxynucleotides Designed to Form DNA Triple Helices, The Journal of Biol. Chem., 267(8):5712-5721 (1992).

Benimetskaya et al., "Formation of a G-Tetrad and Higher Order Structures Correlated with Biological Activity of the ReIA (NF-KBp65) 'Antisense' Oligodeoxynucleotide", Nucleic Acids Res., 25(13):2648-2656 (1997).

Bock et al., "Selection of Single-Stranded DNA Molecules that Bind and Inhibit Human Thrombin", Nature, 355:564-566 (1992).

Padmanabhan et al., "The Structure of a-Thrombin Inhibited by a 15-Mer Single-Stranded DNA Aptamer", J. Biol. Chem., 268(24):17651-17654 (1993).

Hunziker et al., "Nucleic Acid Analogues: Synthesis and Properties", Mod. Syn. Methods, 7:331-417 (1995).

Crooke et al., "Progress in Antisense Oligonucleotide Therapeutics", Ann. Rev. Pharm. Tox., 36:107-129 (1996).

Remington's Pharmaceutical Sciences, 18m Edition, ed. A. Gennaro, Mack Publishing Co., PA (1990).

Rando et al., Suppression of Human Immunodeficiency Virus Type 1 Activity in Vitro by Oligonucleotides which Form Intramolecular Tetrads, the Journal of Biol. Chem., 270(4):1754-1760 (1995).

* cited by examiner

FIG. 1a

Serum total cholesterol levels (mg/dl ± SD)

| Week | PBS | TLR Antagonist | | Lipitor® |
|---|---|---|---|---|
| | | 5 mg/kg | 20 mg/kg | |
| 6 | 145 ± 6 | 135 ± 16 | 155 ± 1 | 140 ± 6 |
| 8 | 185 ± 2 | 167 ± 1 | 132 ± 7 | 164 ± 1 |
| 10 | 197 ± 8 | 177 ± 5 | 145 ± 3 | 182 ± 5 |
| 12 | 234 ± 11 | 179 ± 7 | 162 ± 8 | 189 ± 23 |

FIG. 1b

% Change over week 6

| Week | PBS | TLR Antagonist | | Lipitor® |
|---|---|---|---|---|
| | | 5 mg/kg | 20 mg/kg | |
| 8 | 28 | 24 | -15 | 17 |
| 10 | 36 | 31 | -7 | 30 |
| 12 | 61 | 32 | 5 | 35 |

FIG. 2a

C57BL/6 mice serum analysis

| Week | Chol, mg/dl PBS | Chol, mg/dl Anta | HDL, mg/dl PBS | HDL, mg/dl Anta | LDL mg/dl PBS | LDL mg/dl Anta | TG, mg/dl PBS | TG, mg/dl Anta | Glucose, mg/dl PBS | Glucose, mg/dl Anta | HDL-C/LDL-C PBS | HDL-C/LDL-C Anta |
|---|---|---|---|---|---|---|---|---|---|---|---|---|
| 6  | 81  | 82  | 59 | 57 | 5  | 3  | 86  | 108 | 149 | 159 | 11.8 | 19  |
| 7  | 114 | 104 | 86 | 77 | 7  | 13 | 105 | 72  | 184 | 163 | 12.3 | 5.9 |
| 8  | 91  | 75  | 77 | 55 | 5  | 6  | 42  | 72  | 128 | 62  | 15.4 | 9.2 |
| 9  | 84  | 84  | 70 | 72 | 6  | -  | 40  | 49  | 70  | 47  | 11.7 | --  |
| 10 | 122 | 62  | 96 | 41 | 15 | 14 | 55  | 37  | 119 | 117 | 6.4  | 2.9 |
| 11 | 95  | 62  | 85 | 47 | -  | 7  | 55  | 41  | 53  | 85  | --   | 6.7 |
| 12 | 101 | 60  | 91 | 46 | -  | 6  | 64  | 40  | 48  | 86  | --   | 7.7 |

FIG. 2b

57BL/6 mice serum: % Change

| Week | Chol, mg/dl PBS | Anta | HDL, mg/dl PBS | Anta | LDL, mg/dl PBS | Anta | TG, mg/dl PBS | Anta | Glucose, mg/dl PBS | Anta |
|---|---|---|---|---|---|---|---|---|---|---|
| 7 | 40.7 | 26.8 | 45.7 | 35.1 | 40 | 333.3 | 22.1 | -33.3 | 23.5 | 2.5 |
| 8 | 12.3 | -8.5 | 30.5 | -3.5 | 0 | 100 | -45.3 | -33.3 | 14.1 | -61 |
| 9 | 3.7 | 2.4 | 18.6 | 26.3 | 20 | -100 | -53.5 | -54.6 | -53 | -70.4 |
| 10 | 50.6 | -24.4 | 62.7 | -28.1 | 200 | 366.7 | -36.1 | -65.7 | -20.1 | -26.4 |
| 11 | 17.3 | -24.4 | 44.1 | -17.5 | -100 | 133.3 | -36.1 | -62 | -64.4 | -46.5 |
| 12 | 24.7 | -26.8 | 54.2 | -19.3 | -100 | 100 | -25.6 | -63 | -67.8 | -45.9 |

FIG. 2c

ApoE-deficient mice serum analysis

| Week | Chol, mg/dl PBS | Chol, mg/dl Anta | HDL, mg/dl PBS | HDL, mg/dl Anta | LDL, mg/dl PBS | LDL, mg/dl Anta | TG, mg/dl PBS | TG, mg/dl Anta | Glucose, mg/dl PBS | Glucose, mg/dl Anta | HDL-C/LDL-C PBS | HDL-C/LDL-C Anta |
|---|---|---|---|---|---|---|---|---|---|---|---|---|
| 6  | 458  | 461 | 102 | 105 | 335  | 335 | 103 | 103 | 178 | 174 | 0.3  | 0.3  |
| 7  | 1161 | 951 | 357 | 318 | 782  | 609 | 110 | 119 | 179 | 153 | 0.45 | 0.52 |
| 8  | 1068 | 963 | 360 | 321 | 694  | 630 | 68  | 62  | 49  | 59  | 0.52 | 0.51 |
| 9  | 1008 | 948 | 315 | 312 | 683  | 626 | 50  | 50  | 54  | 86  | 0.46 | 0.5  |
| 10 | 1026 | 590 | 369 | 207 | 646  | 380 | 54  | 48  | 134 | 88  | 0.57 | 0.54 |
| 11 | 990  | 585 | 318 | 225 | 650  | 352 | 108 | 41  | 159 | 89  | 0.49 | 0.64 |
| 12 | 1596 | 624 | 396 | 225 | 1170 | 391 | 151 | 41  | 160 | 71  | 0.34 | 0.56 |

FIG. 2d

ApoE-deficient mice: % Change

| Week | Chol, mg/dl PBS | Chol, mg/dl Anta | HDL, mg/dl PBS | HDL, mg/dl Anta | LDL, mg/dl PBS | LDL, mg/dl Anta | TG, mg/dl PBS | TG, mg/dl Anta | Glucose, mg/dl PBS | Glucose, mg/dl Anta |
|---|---|---|---|---|---|---|---|---|---|---|
| 7 | 153.5 | 106.3 | 250 | 202.9 | 133.4 | 81.8 | 6.8 | 15.5 | 0.6 | -12.1 |
| 8 | 133.2 | 108.9 | 252.9 | 205.7 | 107.1 | 88.1 | -34 | -39.8 | -72.5 | -66.1 |
| 9 | 120.1 | 105.6 | 208.8 | 197.4 | 103.9 | 86.9 | -51.5 | -51.5 | -69.7 | -50.6 |
| 10 | 124 | 28 | 261.8 | 97.1 | 92.8 | 13.4 | -47.6 | -53.4 | -24.7 | -49.4 |
| 11 | 116.2 | 26.9 | 211.8 | 114.3 | 94 | 5.1 | 4.9 | -60.2 | -10.7 | -48.9 |
| 12 | 248.5 | 35.4 | 288.2 | 114.3 | 249.3 | 16.7 | 46.6 | -60.2 | -10.1 | -59.2 |

USE OF INHIBITORS OF TOLL-LIKE RECEPTORS IN THE PREVENTION AND TREATMENT OF HYPERCHOLESTEROLEMIA AND HYPERLIPIDEMIA AND DISEASES RELATED THERETO

This application claims the benefit of priority from U.S. Provisional Patent Application No. 61/102,974, filed on Oct. 6, 2008, the disclosure of which is explicitly incorporated by reference herein.

BACKGROUND OF THE INVENTION

1. Field of the Invention

The present invention is related to the use of compounds and pharmaceutical compositions that inhibit the Toll-Like Receptor signaling pathway to prevent or treat diseases or disorders. The invention further relates to the treatment of hypercholesterolemia and hyperlipidemia and diseases related thereto.

2. Summary of the Related Art

Due to their insolubility in blood, cholesterol and lipids are transported in the circulatory system in lipoproteins. Cholesterol and lipid in lipoproteins can be deposited in tissues throughout the circulatory system. High concentrations of cholesterol (hypercholesterolemia) and/or lipid (hyperlipidemia) in the circulatory system are conditions known to be associated with many diseases, including, but not limited to, coronary heart disease, arteriosclerosis, atherosclerosis, stroke, peripheral vascular disease, diabetes and high blood pressure. It has been established that lowering low density lipoprotein lipid and/or low density lipoprotein cholesterol concentration in the blood is beneficial for protecting against diseases associated with high blood concentrations of cholesterol and/or lipids. It has been further established that increasing the concentration of high density lipoprotein lipid and/or high density lipoprotein cholesterol concentration in relation to the concentration of low density lipoprotein lipid and/or low density lipoprotein cholesterol concentration in the blood is beneficial for protecting against diseases associated with high blood concentrations of cholesterol and/or lipids.

Toll-like receptors (TLRs) are present on many cells of the immune system and have been shown to be involved in the innate immune response (Hornung, V. et al. (2002) *J. Immunol.* 168:4531-4537). TLRs are a key means by which mammals recognize and mount an immune response to foreign molecules and also provide a means by which the innate and adaptive immune responses are linked (Akira, S. et al. (2001) *Nature Immunol.* 2:675-680; Medzhitov, R. (2001) *Nature Rev. Immunol.* 1:135-145). In mammals, this family consists of at least eleven proteins called TLR1 to TLR11, which are known to recognize pathogen associated molecular patterns (PAMPs) from bacteria, fungi, parasites and viruses and induce an immune response mediated by a number of transcription factors (Poltorak, A. et al. (1998) *Science* 282:2085-2088; Underhill, D. M., et al. (1999) *Nature* 401:811-815; Hayashi, F. et al. (2001) *Nature* 410:1099-1103; Zhang, D. et al. (2004) *Science* 303:1522-1526; Meier, A. et al. (2003) *Cell. Microbiol.* 5:561-570; Campos, M. A. et al. (2001) *J. Immunol.* 167: 416-423; Hoebe, K. et al. (2003) *Nature* 424: 743-748; Lund, J. (2003) *J. Exp. Med.* 198:513-520; Heil, F. et al. (2004) *Science* 303:1526-1529; Diebold, S. S., et al. (2004) *Science* 303:1529-1531; Hornung, V. et al. (2004) *J. Immunol.* 173:5935-5943). TLRs are known to be a key means by which mammals recognize and mount an immune response to foreign molecules and are also recognized as providing a means by which the innate and adaptive immune responses are linked (Akira, S. et al. (2001) *Nature Immunol.* 2:675-680; Medzhitov, R. (2001) *Nature Rev. Immunol.* 1:135-145).

Some TLRs are located on the cell surface to detect and initiate a response to extracellular pathogens and other TLRs are located inside the cell to detect and initiate a response to intracellular pathogens. Table 1 provides a representation of TLRs, the known agonists therefore and the cell types known to contain the TLR (Diebold, S. S. et al. (2004) *Science* 303:1529-1531; Liew, F. et al. (2005) *Nature* 5:446-458; Hemmi H et al. (2002) *Nat. Immunol.* 3:196-200; Jurk M et al. (2002) *Nat. Immunol.* 3:499; Lee J et al. (2003) *Proc. Natl. Acad. Sci. USA* 100:6646-6651); (Alexopoulou, L. (2001) *Nature* 413:732-738).

TABLE 1

| TLR Molecule | Agonist | Cell Types Containing Receptor |
|---|---|---|
| Cell Surface TLRs: | | |
| TLR2 | bacterial lipopeptides | Monocytes/macrophages, Myeloid dendritic cells, Mast cells |
| TLR4 | gram negative bacteria | Monocytes/macrophages, Myeloid dendritic cells, Mast cells, Intestinal epithelium |
| TLR5 | motile bacteria | Monocyte/macrophages, Dendritic cells, Intestinal epithelium |
| TLR6 | gram positive bacteria | Monocytes/macrophages, Mast cells, B lymphocytes |
| Endosomal TLRs: | | |
| TLR3 | double stranded RNA viruses | Dendritic cells, B lymphocytes |
| TLR7 | single stranded RNA viruses; RNA-immunoglobulin complexes | Monocytes/macrophages, Plasmacytoid dendritic cells, B lymphocytes |
| TLR8 | single stranded RNA viruses; RNA-immunoglobulin complexes | Monocytes/macrophages, Dendritic cells, Mast cells |
| TLR9 | DNA containing unmethylated "CpG" motifs; DNA-immunoglobulin complexes | Monocytes/macrophages, Plasmacytoid dendritic cells, B lymphocytes |

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g., viral infections, intracellular pathogens, and tumor cells), and results in a secretion of IFN-gamma and a concomitant activation of CTLs.

As a result of their involvement in regulating an inflammatory response, activation of TLRs has been shown to play a role in the pathogenesis of many diseases, including autoimmunity, infectious disease and inflammation (Papadimitraki et al. (2007) *J. Autoimmun.* 29: 310-318; Sun et al. (2007) *Inflam. Allergy Drug Targets* 6:223-235; Diebold (2008) *Adv. Drug Deliv. Rev.* 60:813-823; Cook, D. N. et al. (2004) *Nature Immunol.* 5:975-979; Tse and Horner (2008) *Semin. Immu-* nopathol. 30:53-62; Tobias & Curtiss (2008) *Semin. Immunopathol.* 30:23-27; Ropert et al. (2008) *Semin. Immunopathol.* 30:41-51; Lee et al. (2008) *Semin. Immunopathol.* 30:3-9; Gao et al. (2008) *Semin. Immunopathol.* 30:29-40; Vijay-Kumar et al. (2008) *Semin. Immunopathol.* 30:11-21). As a result of their role in inflammation, it is recognized that down-regulating TLR expression and/or activity may provide a useful means for disease intervention.

To date, investigative strategies aimed at selectively inhibiting TLR activity have involved small molecules (e.g., chloroquine and hydroxychloroquine) (see, for example, WO 2005/007672 and Krieg, A. M. (2002) *Annu. Rev. Immunol.* 20:709), antibodies (see, for example, Duffy, K. et al. (2007) *Cell Immunol.* 248:103-114), catalytic RNAi technologies (e.g., small inhibitory RNAs), cyclohexene derivatives (Il et al. (2006) *Mol. Pharmcol.* 69:1288-1295), lipid derivatives (Akira et al. (2005) *Circulation* 114:270-274, oligonucleotides containing poly-G sequences (Pawar et al. (2007) *J. Am. Soc. Nephrol.* 18:1721-1731) and competitive inhibition with methylated or modified oligonucleotides (see, for example, Barrat and Coffman (2008) Immunol. Rev. 223: 271-283). Passages of these publications disclosing TLR inhibitors are specifically incorporated by reference.

As a result of their ability to inhibit a TLR-mediated inflammatory response, TLR antagonists are currently being investigated as possible therapeutics for the treatment and/or prevention of certain diseases. However, the role of TLRs in regulating blood cholesterol concentration and/or blood lipid concentration and/or the diseases associated therewith was heretofore unknown.

BRIEF SUMMARY OF THE INVENTION

The present inventors have surprisingly discovered that inhibition of TLR pathway signaling can lower blood cholesterol concentration and/or blood lipid concentration and/or increase the ratio of HDL-C to LDL-C in a mammal having elevated blood cholesterol and/or blood lipid.

Thus, in a first aspect, the invention provides methods for lowering blood cholesterol concentration and/or blood lipid concentration in a mammal having elevated blood cholesterol and/or blood lipid by inhibiting TLR signaling. In certain preferred embodiments, TLR signaling is inhibited by inhibiting the expression or activity of one or more TLR or a downstream protein in the TLR signaling pathway, such as the myeloid differentiation marker 88 (MyD88), IL-1R-associated kinase (IRAK), interferon regulating factor (IRF), TNF-receptor-associated factor (TRAF), transforming growth factor beta (TGFβ)-activated kinase1, IκB kinases, IκB, and NF-κB. Thus, in some embodiments inhibition of TLR signaling is achieved by administering to a mammal having elevated blood cholesterol and/or blood lipid a TLR antagonist compound. Certain of these TLR antagonist compounds or compositions are small molecules, for example, but not limited to chloroquine or hydroxychloroquine; antibodies; cyclohexene derivatives; lipid derivatives; synthetic oligonucleotides comprising two triplet sequences, a "CCT" triplet and a "GGG" triplet, in which the "CCT" triplet may be considered proximal and the "GGG" triplet may be considered distal; synthetic oligonucleotides comprising regions that contain "GGG" and/or "GGGG" and/or "GC" sequences, in which multiple of such sequences may be present; synthetic oligonucleotides that are methylated; or synthetic, immune inhibitory oligonucleotides, which may have one or more chemical modifications in the sequence flanking an immune stimulatory motif and/or in an oligonucleotide motif that would be immune stimulatory but for the modification. In some embodiments, TLR signaling is inhibited by inhibiting the expression of one or more TLR or a downstream protein in the TLR signaling pathway, such as MyD88, IRAK, IRF, TRAF, TGFβ, IκB kinase, IκB, and NF-κB using gene expression blocking technologies such as antisense oligonucleotides, decoy RNAs, ribozymes, catalytic RNAi technologies, siRNA or miRNA.

In some preferred embodiments, the method of lowering blood cholesterol concentration and/or blood lipid concentration in a mammal having elevated blood cholesterol and/or blood lipid comprises administering to the mammal a TLR antagonist composition having the structure 5'-$N_m$—$N_3N_2N_1CGN^1N^2N^3$—$N^m$-3', wherein CG is an oligonucleotide motif and C is cytosine or a pyrimidine nucleotide derivative, and G is guanosine or a purine nucleotide derivative; $N_1$-$N_3$ and $N^1$-$N^3$, at each occurrence, is independently a nucleotide or nucleotide derivative; $N_m$ and $N^m$, at each occurrence, is independently a nucleotide, nucleotide derivative or non-nucleotide linkage; provided that at least one $N_1$-$N_3$ and/or $N^1$-$N^3$ and/or C and/or G is a nucleotide derivative wherein the oligonucleotide motif would be immune stimulatory but for the nucleotide derivative; and wherein m is an integer from 0 to about 30.

In a further embodiment, the invention provides a method of lowering blood cholesterol concentration and/or blood lipid concentration in a mammal having elevated blood cholesterol and/or blood lipid comprising administering to the mammal a TLR antagonist composition having the structure 5'-$N_m$—$N_3N_2N_1CGN^1N^2N^3$—$N^m$-3', wherein CG is an oligonucleotide motif and C is cytosine or a pyrimidine nucleotide derivative, and G is guanosine or a purine nucleotide derivative; $N_1$-$N_3$ and $N^1$-$N^3$, at each occurrence, is independently a nucleotide or a nucleotide derivative; $N_m$ and $N^m$, at each occurrence, is independently a nucleotide, nucleotide derivative or non-nucleotide linkage; provided that at least one $N_1$-$N_3$ and/or $N^1$-$N^3$ and/or C and/or G is a nucleotide derivative; and further provided that compound may contain less than 3 consecutive guanosine nucleotides wherein the oligonucleotide motif would be immune stimulatory but for the nucleotide derivative or non-nucleotide linkage; and wherein m is an integer from 0 to about 30.

In another embodiment, the invention provides for a method of lowering blood cholesterol concentration and/or blood lipid concentration in a mammal having elevated blood cholesterol and/or blood lipid through administration of a pharmaceutical composition comprising one or more TLR antagonist compounds or compositions and a pharmaceutically acceptable carrier.

In some preferred embodiments, lowering blood cholesterol concentration and/or blood lipid concentration in a mammal having elevated blood cholesterol and/or blood lipid comprises administering one or more TLR antagonists compounds, wherein the TLR is selected from TLR2, TLR3, TLR4, TLR5, TLR7, TLR8 and TLR9.

In a second aspect, the invention provides a method for therapeutically treating a disease associated with high blood lipid concentration and/or high blood cholesterol concentration in a mammal, such method comprising inhibiting TLR signaling in the mammal. In some embodiments, TLR signaling is inhibited by administering to the mammal one or more TLR antagonist compounds according to the invention in a pharmaceutically effective amount. In some embodiments TLR signaling is inhibited by inhibiting the expression of one or more TLR, or another protein in the TLR signaling pathway in a pharmaceutically effective amount. In certain preferred embodiments of this aspect of the invention, the disease is hypercholesterolemia, hyperlipidemia, coronary heart disease, arteriosclerosis, atherosclerosis, stroke, peripheral vascular disease, diabetes or high blood pressure.

In a third aspect, the invention provides a method for preventing a disease associated with high blood lipid concentration and/or blood cholesterol concentration in a mammal having elevated blood cholesterol and/or blood lipid, such method comprising inhibiting TLR signaling in the mammal. In some embodiments, TLR signaling is inhibited by administering to the mammal one or more TLR antagonist compounds according to the invention in a pharmaceutically effective amount. In some embodiments TLR signaling is inhibited by inhibiting the expression of one or more TLR, or another protein in the TLR signaling pathway. In certain preferred embodiments, the disease is hypercholesterolemia, hyperlipidemia, coronary heart disease, arteriosclerosis, atherosclerosis, stroke, peripheral vascular disease, diabetes or high blood pressure.

In some embodiments, the methods according to the invention further comprise administering to the mammal one or more cholesterol lowering compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof.

BRIEF DESCRIPTION OF THE DRAWINGS

FIG. 1a depicts the total serum cholesterol in animals treated according to Example 2. Briefly, animals were fed a Western diet and administered a TLR antagonist (5 mg/kg or 20 mg/kg), PBS or Lipitor® (20 mg/kg) for 12 weeks. Blood samples were collected over the course of the twelve-week study and used for determining total serum cholesterol. These data demonstrate that administration of a TLR antagonist can inhibit a rise in total serum cholesterol following in vivo administration.

FIG. 1b depicts the percent change in total serum cholesterol over time, in animals treated according to Example 2. Briefly, animals were fed a Western diet and administered a TLR antagonist (5 mg/kg or 20 mg/kg), PBS or Lipitor® (20 mg/kg) for 12 weeks. Blood samples were collected over the course of the twelve-week study and used for determining total serum cholesterol. These data demonstrate that a TLR antagonist can inhibit a rise in total serum cholesterol following in vivo administration.

FIG. 2a depicts total serum cholesterol, high density lipoprotein (HDL), low density lipoprotein (LDL), triglyceride (TG), glucose, and the ratio of HDL-cholesterol to LDL-cholesterol (HDL-C/LDL-C) in animals treated according to Example 3. Briefly, C57/BL/6 mice were fed a Western diet and administered a TLR antagonist (5 mg/kg or 20 mg/kg) or PBS for 12 weeks. Blood samples were collected over the course of the twelve-week study and used for determining total serum cholesterol, HDL, LDL, TG and glucose concentrations. These data demonstrate that a TLR antagonist can inhibit a rise in total serum cholesterol, LDL and TG and maintain or lower blood glucose concentrations following in vivo administration.

FIG. 2b depicts the percent changes in total serum cholesterol, high density lipoprotein (HDL), low density lipoprotein (LDL), triglyceride (TG), and glucose in animals treated according to Example 3.

FIG. 2c depicts total serum cholesterol, high density lipoprotein (HDL), low density lipoprotein (LDL), triglyceride (TG), glucose, and the ratio of HDL-cholesterol to LDL-cholesterol (HDL-C/LDL-C) in animals treated according to Example 3. Briefly, ApoE-deficient mice were fed a Western diet and administered a TLR antagonist (5 mg/kg or 20 mg/kg) or PBS for 12 weeks. Blood samples were collected over the course of the twelve-week study and used for determining total serum cholesterol, HDL, LDL, TG and glucose concentrations. These data demonstrate that a TLR antagonist can inhibit a rise in total serum cholesterol, LDL, TG and maintain or lower blood glucose concentrations following in vivo administration to mammals with a predisposition to developing hypercholesterolemia and/or hyperlipidemia.

FIG. 2d depicts the percent changes in total serum cholesterol, high density lipoprotein (HDL), low density lipoprotein (LDL), triglyceride (TG), and glucose in animals treated according to Example 3.

DETAILED DESCRIPTION OF THE PREFERRED EMBODIMENTS

Figure 3A:
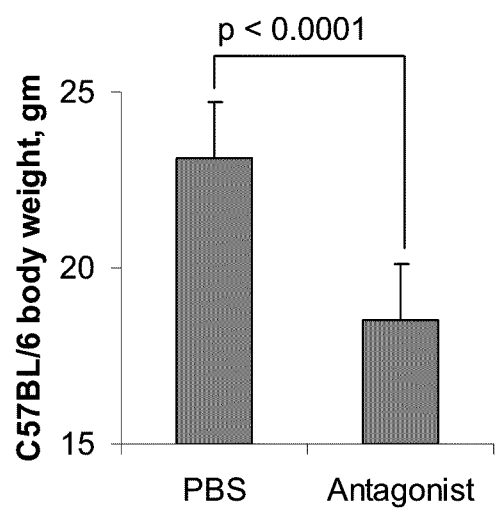
FIG. 3a depicts total body weight in animals treated according to Example 3. Briefly, C57/BL/6 mice were fed a Western diet and administered a TLR antagonist (5 mg/kg or 20 mg/kg) or PBS for 12 weeks. Body weight was measured over the course of the twelve-week study. These data demonstrate that a TLR antagonist can inhibit a rise in total body weight following in vivo administration to mammals fed a high fat diet.
Figure 3B:
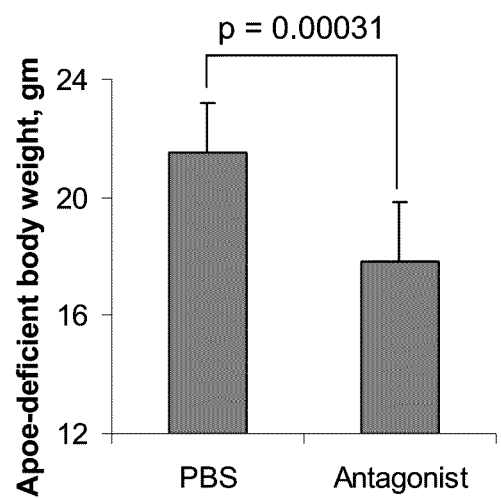
FIG. 3b depicts total body weight in animals treated according to Example 3. Briefly, ApoE-deficient mice were fed a Western diet and administered a TLR antagonist (5 mg/kg or 20 mg/kg) or PBS for 12 weeks. Body weight was measured over the course of the twelve-week study. These data demonstrate that a TLR antagonist can inhibit a rise in total body weight following in vivo administration to mammals with a predisposition to developing hypercholesterolemia and/or hyperlipoproteinemia that are fed a high fat diet.

The present invention relates to the therapeutic use of TLR antagonists to inhibit and/or suppress hypercholesterolemia and/or hyperlipidemia and/or the diseases associated therewith. The present inventors have surprisingly discovered that inhibition of TLR pathway signaling can lower blood cholesterol concentration and/or blood lipid concentration in a mammal having elevated blood cholesterol and/or blood lipid.

Thus, in a first aspect, the invention provides methods for lowering blood cholesterol concentration and/or blood lipid concentration in a mammal having elevated blood cholesterol and/or blood lipid by inhibiting TLR signaling. In certain preferred embodiments, TLR signaling is inhibited by inhibiting the expression or activity of one or more TLR or a downstream protein in the TLR signaling pathway, such as MyD88, IRAK, IRF, TRAF, TGFβ, IκB kinase, IκB, and NF-κB. Thus, in some embodiments inhibition of TLR signaling is achieved by administering to a mammal having elevated blood cholesterol and/or blood lipid a TLR antagonist compound. Certain of these TLR antagonist compounds or compositions are small molecules that down-regulate maturation of endosomes, for example, but not limited to chloroquine or hydroxylchloroquine; antibodies; cyclohexene derivatives; lipid derivatives; synthetic oligonucleotides comprising two triplet sequences, a "CCT" triplet and a "GGG" triplet, in which the "CCT" triplet may be considered proximal and the "GGG" triplet may be considered distal; synthetic oligonucleotides comprising regions that contain "GGG" and/or "GGGG" and/or "GC" sequences, in which multiple of such sequences may be present; synthetic oligonucleotides that are methylated; or synthetic, immune inhibitory oligonucleotides, which may have one or more chemical modifications in the sequence flanking an immune stimulatory motif and/or in an oligonucleotide motif that would be immune stimulatory but for the modification. In some embodiments, TLR signaling is inhibited by inhibiting the expression of one or more TLR or a downstream protein in the TLR signaling pathway, such as MyD88, IRAK, IRF, TRAF, TGFβ, IκB kinase, IκB, and/or NF-κB using gene expression blocking technologies such as antisense oligonucleotides, decoy RNAs, ribozymes, catalytic RNAi technologies, siRNA or miRNA. In certain embodiments wherein TLR activity or expression is inhibited, the TLR is selected from TLR2, TLR3, TLR4, TLR5, TLR7, TLR8 and/or TLR9.

Furthermore, the present invention provides TLR antagonist compounds having optimal levels of blood cholesterol concentration and/or blood lipid concentration lowering activity and methods for making and using such compounds.

In addition, inhibition of TLR signaling according to the invention is useful in combination with one or more lipid lowering compounds or compositions, cholesterol lowering compounds or compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof for preventing and/or treating diseases.

Subjects in need of preventing an increase of blood cholesterol and/or lipid concentration and/or treatment of a high blood cholesterol concentration and/or high blood lipid concentration would include, for example, those at risk of having a cardiovascular event.

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In exemplar embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann E et al. (1990) *Chem. Rev.* 90:543; "Protocols for Oligonucleotides and Analogs" *Synthesis and Properties & Synthesis and Analytical Techniques*, S. Agrawal, ed., Humana Press, Totowa, USA 1993; Hunziker, J. et al. (1995) *Mod. Syn. Methods* 7:331-417; and Crooke, S. et al. (1996) *Ann. Rev. Pharm. Tox.* 36:107-129. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides, respectively, having any such internucleoside linkage, whether or not the linkage comprises a phosphate group. In certain preferred embodiments, these internucleoside linkages may be phosphodiester, phosphorothioate or phosphorodithioate linkages, or combinations thereof.

The term "2'-substituted" generally includes nucleosides or in which the hydroxyl group at the 2' position of the pentose moiety is substituted to produce a 2'-substituted or 2'-O-substituted nucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, for example, but not limited to substitution with halo, hydroxy, trifluoromethyl, cyano, nitro, acyl, acyloxy, alkoxy, carboxyl, carboalkoxy or amino groups. Examples of 2'-O-substituted nucleosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5' (upstream) from another region or position in the same polynucleotide or oligonucleotide.

The term "about" generally means that the exact number is not critical. Thus, the number of nucleoside residues in the oligonucleotides according to the invention is not critical, and oligonucleotides having one or two fewer nucleoside residues, or from one to several additional nucleoside residues are contemplated as equivalents of each of the embodiments described above.

The term "agonist" generally refers to a substance that can bind to a receptor and induce a response. Such response may be an increase in the activity mediated by the receptor. An agonist often mimics the action of a naturally occurring substance such as a ligand.

The term "antagonist" generally refers to a substance that can bind to a receptor, but does not produce a biological response upon binding. The antagonist can block, inhibit or attenuate the response mediated by an agonist and may compete with agonists for binding to a receptor. Such antagonist activity may be reversible or irreversible.

The term "antisense oligonucleotide" generally refers to strands of DNA or RNA or combinations thereof that are complementary to a chosen nucleic acid sequence. Such nucleic acid sequence may be in the form of messenger RNA (mRNA). When introduced into an animal or cell, an antisense oligonucleotide can bind to and cause the reduction in the translation of RNA to which it is complementary. If binding takes places, this nucleic acid complex can be degraded by endogenous enzymes. Antisense oligonucleotides include, but are not limited to, traditional antisense oligonucleotides, short interfering RNA (siRNA), micro RNA (mRNA) and ribozymes. Antisense oligonucleotides that would be useful according to the invention include but are not limited to those in Kandimalla et al. (U.S. patent application Ser. Nos. 12/510,469; 12/534,462; 12/534,476; 12/534,911; and 12/537,354; and U.S. Provisional Patent Application Nos. 61/111,143; 61/111,148; and 61/111,160).

The term "small molecule" generally refers to small organic compounds that are biologically active but are not polymers. Small molecules may exist naturally or may be created synthetically. Generally, small molecules do not include proteins or oligonucleotides. Small molecules may include compounds that down-regulate the maturation of endosomes, for example, but not limited to, chloroquine and hydroxychloroquine.

The term "physiologically acceptable" generally refers to a material that does not interfere with the effectiveness of the TLR antagonist compound and that is compatible with a biological system such as a cell, cell culture, tissue, or organism. Preferably, the biological system is a living organism, such as a mammal.

The term "pharmaceutically acceptable" generally refers to compositions that are suitable for use in humans and animals without undue toxicity.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences*, 18th Edition, A. Gennaro, ed., Mack Publishing Co., Easton, Pa., 1990.

The term "co-administration" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The terms an "effective amount," "pharmaceutically effective amount" or "therapeutically effective amount" generally refer to an amount sufficient to affect a desired biological effect, such as beneficial results. Thus, an "effective amount" or "sufficient amount" or "pharmaceutically effective amount" or "therapeutically effective-amount" will depend upon the context in which it is being administered. In the context of administering a composition that modulates an immune response to a co-administered antigen, an effective amount of a TLR antagonist compound and antigen is an amount sufficient to achieve the desired modulation as compared to the immune response obtained when the antigen is administered alone. An effective amount may be administered in one or more administrations.

The term "in combination with" generally means in the course of treating a disease or disorder in a patient, administering a TLR antagonist compound and an agent useful for treating the disease or disorder that does not diminish the immune modulatory effect of the TLR antagonist compound. Such combination treatment may also include more than a single administration of a TLR antagonist compound and/or independently an agent. The administration of the TLR antagonist compound and/or the agent may be by the same or different routes.

The term "individual" or "patient" or "subject" or "mammal" includes a human. Mammals generally include, but are not limited to, humans, non-human primates, rats, mice, cats, dogs, horses, cattle, cows, pigs, sheep and rabbits.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine or uracil. A modified sugar is any sugar that is not ribose or 2' deoxyribose that can be used in the backbone for an oligonucleotide.

The term "inhibiting" or "suppressing" generally refers to a decrease in a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The term "oligonucleotide motif" means an oligonucleotide sequence, including a dinucleotide. An "oligonucleotide motif that would be immune stimulatory, but for one or more modifications [or specifically recited modifications]" means an oligonucleotide motif that is immune stimulatory in a parent oligonucleotide, but not in a derivative oligonucleotide, wherein the derivative oligonucleotide is derived from the parent oligonucleotide by one or more modifications of the parent oligonucleotide.

The terms CpG, C*pG, C*pG* and CpG* refer to oligonucleotide motifs that are immune stimulatory and comprise cytosine or a cytosine analog and a guanine or a guanine analog.

The term "hypercholesterolemia" generally refers to the presence of high levels of cholesterol in the blood. Hypercholesterolemia can be secondary to many diseases and can contribute to many other diseases, including but not limited to cardiovascular disease, atherosclerosis and pancreatitis. Elevated blood cholesterol can be due to elevated levels of lipoproteins, the particles that carry cholesterol and lipids (for example triglycerides) in the bloodstream. Lipoproteins include, for example but not limited to, high density lipoprotein (HDL), low density lipoprotein (LDL) and very low density lipoprotien (VLDL).

The term "hyperlipidemia" generally refers to the presence of elevated or abnormal levels of triglyceride (TG), lipids or lipoproteins in the blood. Elevated or abnormal levels of triglyceride, lipid and lipoprotein are common in the general population. Substantial effort is exerted to normalize the triglyceride, lipid and lipoprotein levels in patients due to the influence of lipid and cholesterol on cardiovascular and other diseases.

The term "statin" generally refers to a class of drugs used to lower cholesterol levels in people with or at risk of developing cardiovascular disease. These compounds lower cholesterol by inhibiting the enzyme HMG-CoA reductase, the rate-limiting enzyme in the pathway of cholesterol synthesis. Many statins are well known in the art and include, without limitation atorvastatin, cerivastatin (rivastatin), fluvastatin, lovastatin, mevastatin, pitavastatin, pravastatin, rosuvastatin, and simvastatin.

The term "treatment" generally refers to an approach intended to obtain a beneficial or desired results, which may include alleviation of symptoms or delaying or ameliorating a disease progression. As such, and without limitation, "treatment" includes palliative treatment and beneficial results that are temporary (i.e., not permanent). For example, cholesterol levels may decrease during treatment according to the invention but eventually increase once treatment is terminated.

In some preferred embodiments, the oligonucleotide comprises an oligonucleotide motif and at least one modification, wherein the oligonucleotide motif would be immune stimulatory (e.g., unmethylated CpG), but for the one or more modifications that suppress the activity of the oligonucleotide motif, provided that compound may contain less than 4 consecutive guanosine nucleotides and preferably less than 3 consecutive guanosine nucleotides. Such modifications may be in the oligonucleotide 5' terminus, in a sequence flanking the oligonucleotide motif, and/or within the oligonucleotide motif. These modifications result in a TLR antagonist compound that suppresses TLR-modulated immune stimulation. Such modifications can be to the bases, sugar residues and/or the phosphate backbone of the nucleotides/nucleosides flanking the oligonucleotide motif or within the oligonucleotide motif. In some embodiments, the modification is a 2'-substitution.

In some embodiments, when the modification is a 2' alkylation or alkoxylation then the modification is not 5' adjacent to the oligonucleotide motif; when the modification is a non-charged internucleoside linkage then the modification is not 5' adjacent to the oligonucleotide motif; and when the modification is a 3' alkylation or alkoxylation then the modification is not 5' or 3' adjacent to the oligonucleotide motif.

In other embodiments of the invention, the TLR antagonist compound is an antisense oligonucleotide.

In some preferred embodiments, the general structure of an oligonucleotide-based TLR antagonist may be represented as, but is not limited to, 5'-$N_m$—$N_3N_2N_1$CG$N^1N^2N^3$—$N^m$-3' wherein CG is an immune stimulatory motif and C is cytosine or a pyrimidine nucleotide derivative, and G is guanosine or a purine nucleotide derivative; $N_1$-$N_3$ and $N^1$-$N^3$, at each occurrence, is independently a nucleotide or a nucleotide derivative; $N_m$ and $N^m$, at each occurrence, is independently a nucleotide, nucleotide derivative or non-nucleotide linker; provided that at least one $N_1$-$N_3$ and/or $N^1$-$N^3$ and/or C and/or G is a nucleotide derivative; and further provided that compound may contain less than 4 consecutive guanosine nucleotides and preferably less than 3 consecutive guanosine nucleotides, wherein the immune stimulatory activity of the CG is suppressed by the nucleotide derivative or non-nucleotide linker; and wherein m is an integer from 0 to about 30. Such oligonucleotide-based TLR antagonists are disclosed in U.S. application Ser. No. 11/549,048 (U.S. Patent Application Publication No. 2009/0060898), the disclosure of which is explicitly incorporated by reference herein (to the extent that there are any inconsistencies between the instant application and U.S. application Ser. No. 11/549,048, such inconsistencies shall be resolved in accordance with the instant application).

In additional preferred embodiments, the oligonucleotide-based TLR antagonist may contain a modified immune stimulatory motif and may be represented as, but is not limited to, the structure 5'-$N_m$—$N_3N_2N_1$CG$N^1N^2N^3$—$N^m$-3', wherein CG is the modified immune stimulatory motif and C is cytosine, or a pyrimidine nucleotide derivative selected from 5-methyl-dC, 2'-O-substituted-C, 2'-O-methyl-C, 2'-O-methoxyethyl-C, 2'-O-methoxyethyl-5- methyl-C, and 2'-O-methyl-5-methyl-C, and G is guanosine or a purine nucleotide derivative selected from 2'-O-substituted-G, 2'-O-methyl-G, and 2'-O-methoxyethyl-G; $N_1$-$N_3$ and $N^1$-$N^3$, at each occurrence, is independently a nucleotide, nucleotide derivative or non-nucleotide linkage; $N_m$ and $N^m$, at each occurrence, is independently a nucleotide, nucleotide derivative or non-nucleotide linkage; provided that at least one C and/or G of the modified immune stimulatory motif is a nucleotide derivative specified above; and optionally containing less than 3 consecutive guanosine nucleotides; wherein the modified immune stimulatory motif would be immune stimulatory but for the nucleotide derivative; and wherein m is an integer from 0 to about 30. Such oligonucleotide-based TLR antagonists are disclosed in U.S. Provisional Application No. 61/182,928, the disclosure of which is explicitly incorporated by reference herein (to the extent that there are any inconsistencies between the instant application and U.S. Provisional Application No. 61/182,928, such inconsistencies shall be resolved in accordance with the instant application).

In further embodiments of this aspect of the invention, the oligonucleotide-based TLR antagonist containing a modified immune stimulatory motif comprises one or more modified immune stimulatory motifs, wherein CG is the modified immune stimulatory motif and C is cytosine, or a pyrimidine nucleotide derivative selected from 5-methyl-dC, 2'-O-substituted-C, 2'-O-methyl-C, 2'-O-methoxyethoxy-C, 2'-O-methoxyethyl-5-methyl-C, 2'-O-methyl-5-methyl-C, and G is guanosine or a purine nucleotide derivative selected from 2'-O-substituted-G, 2'-O-methyl-G, and 2'-O-methoxyethoxy-G; provided that at least one C and/or G of the modified immune stimulatory motif is a nucleotide derivative specified above; and optionally containing less than 3 consecutive guanosine nucleotides; wherein the modified immune stimulatory motif would be immune stimulatory but for the nucleotide derivative.

In certain embodiments of the invention, the TLR antagonist compounds may comprise at least two oligonucleotides covalently linked by a nucleotide linkage, or a non-nucleotide linker, at their 5'-, 3'- or 2'-ends or by functionalized sugar or by functionalized nucleobase via a non-nucleotide linker or a nucleotide linkage. Such TLR antagonist compounds may be linear or branched. As a non-limiting example, the linker may be attached to the 3'-hydroxyl. In such embodiments, the linker comprises a functional group, which is attached to the 3'-hydroxyl by means of a phosphate-based linkage like, for example, phosphodiester, phosphorothioate, phosphorodithioate, methylphosphonate, or by non-phosphate-based linkages. Possible sites of conjugation for the nucleotide are indicated in Formula I, below, wherein B represents a heterocyclic base and wherein the arrow pointing to P indicates any attachment to phosphorous.

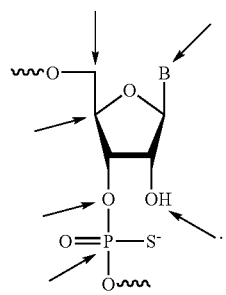

Formula I

In some embodiments, the non-nucleotide linker is a small molecule linker, macromolecule or biomolecule, including, without limitation, polypeptides, antibodies, lipids, antigens, allergens, and oligosaccharides. In some other embodiments, the non-nucleotidic linker is a small molecule linker. For purposes of the invention, a small molecule linker is an organic moiety having a molecular weight of less than 1,000 Da. In some embodiments, the small molecule has a molecular weight of less than 750 Da.

In some embodiments, the small molecule linker is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule linker can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule linker" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, triethylene glycol hexaethylene glycol, polyethylene glycollinkers (e.g., [-O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotide linker may include, but is not limited to, those listed in Table 2, wherein the oligonucleotide-based TLR antagonist is linked through a hydroxyl group present on the non-nucleotidic linker.

TABLE 2

Representative Non-Nucleotidic Linkers

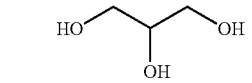

Glycerol (1,2,3-Propanetriol)

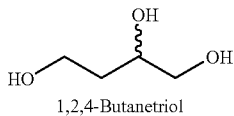

1,2,4-Butanetriol

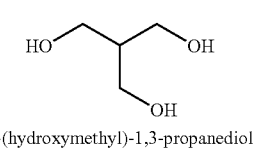

2-(hydroxymethyl)-1,3-propanediol

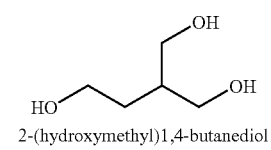

2-(hydroxymethyl)1,4-butanediol

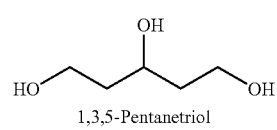

1,3,5-Pentanetriol

TABLE 2-continued

Representative Non-Nucleotidic Linkers

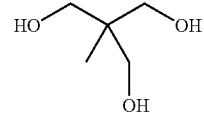

1,1,1-Tris(hydroxymethyl)ethane

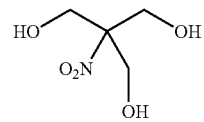

1,1,1-Tris(hydroxymethyl)nitromethane

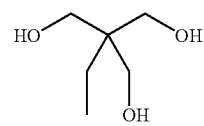

1,1,1-Tris(hydroxymethyl)propane

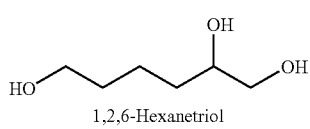

1,2,6-Hexanetriol

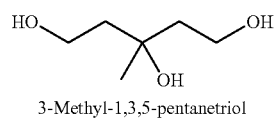

3-Methyl-1,3,5-pentanetriol

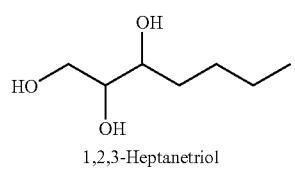

1,2,3-Heptanetriol

2-Amino-2-(hydroxymethyl)-1,3-propanediol

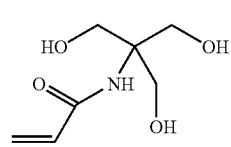

N-[Tris(hydroxymethyl)methyl]acrylamide

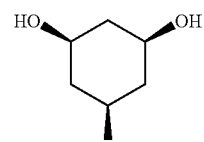

cis-1,3,5-Cyclohexanetriol

TABLE 2-continued

Representative Non-Nucleotidic Linkers

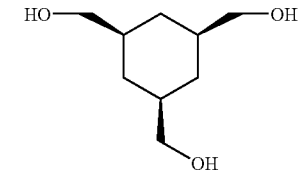

cis-1,3,5-Tri(hydroxymethyl)cyclohexane

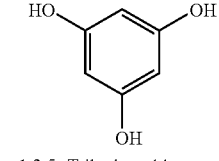

1,3,5,-Trihydroxyl-benzene

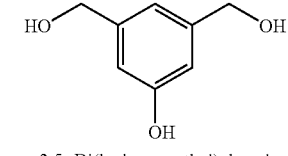

3,5,-Di(hydroxymethyl)phenol

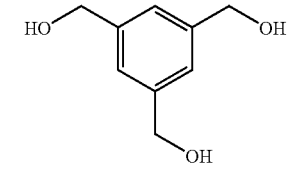

1,3,5,-Tri(hydroxymethyl)benzene

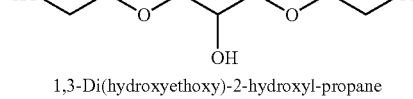

1,3-Di(hydroxyethoxy)-2-hydroxyl-propane

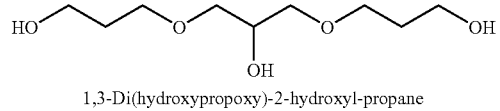 [SMILES: OCCCOCC(O)COCCCO]

1,3-Di(hydroxypropoxy)-2-hydroxyl-propane

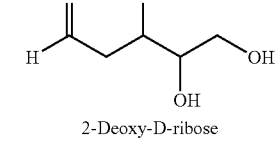

2-Deoxy-D-ribose

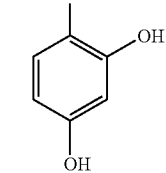

1,2,4-Trihydroxyl-benzene

TABLE 2-continued

Representative Non-Nucleotidic Linkers

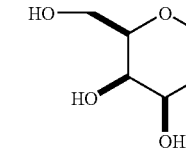

D-Galactoal

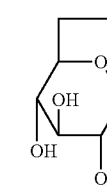

1,6-anhydro-β-D-Glucose

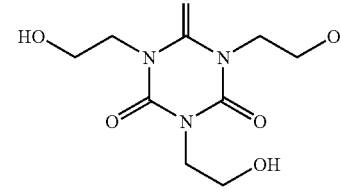

1,3,5-Tris(2-hydroxyethyl)-Cyanuric acid

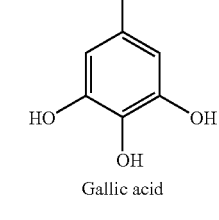

Gallic acid

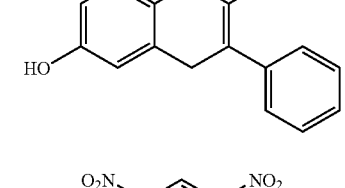

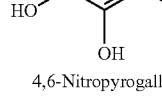

4,6-Nitropyrogallol

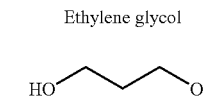

Ethylene glycol

HO⏜OH 1,3-Propanediol

TABLE 2-continued

Representative Non-Nucleotidic Linkers

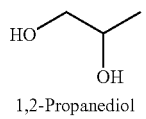
1,2-Propanediol

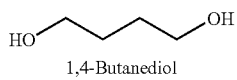
1,4-Butanediol

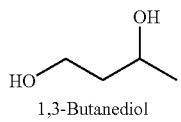
1,3-Butanediol

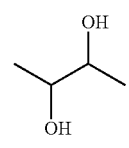
2,3-Butanediol

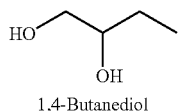
1,4-Butanediol

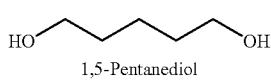
1,5-Pentanediol

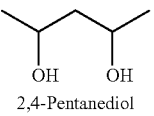
2,4-Pentanediol

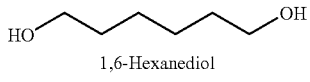
1,6-Hexanediol

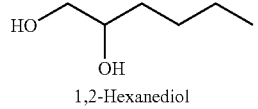
1,2-Hexanediol

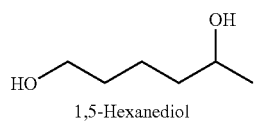
1,5-Hexanediol

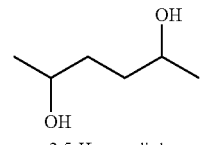
2,5-Hexanediol

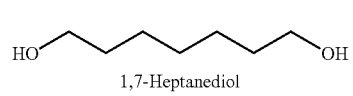
1,7-Heptanediol

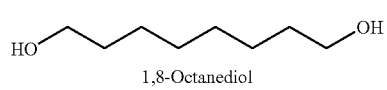
1,8-Octanediol

TABLE 2-continued

Representative Non-Nucleotidic Linkers

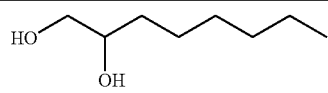
1,2-Octanediol

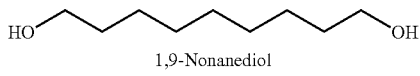
1,9-Nonanediol

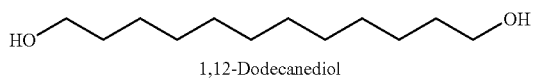 [SMILES: OCCCCCCCCCCCCO]
1,12-Dodecanediol

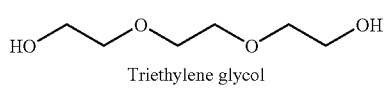
Triethylene glycol

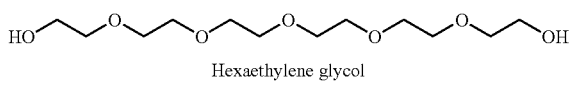
Tetraethylene glycol

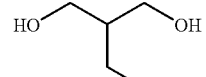
Hexaethylene glycol

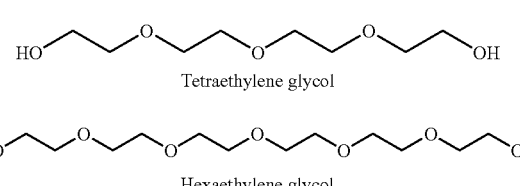
2-(1-Aminopropyl)-1,3-propanediol

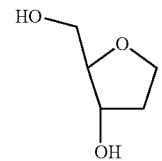
1,2-Dideoxyribose

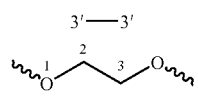

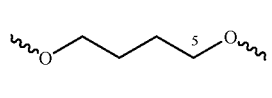

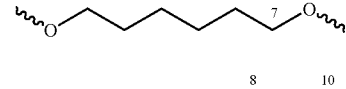

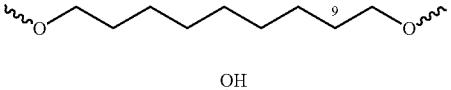

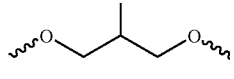

TABLE 2-continued

Representative Non-Nucleotidic Linkers

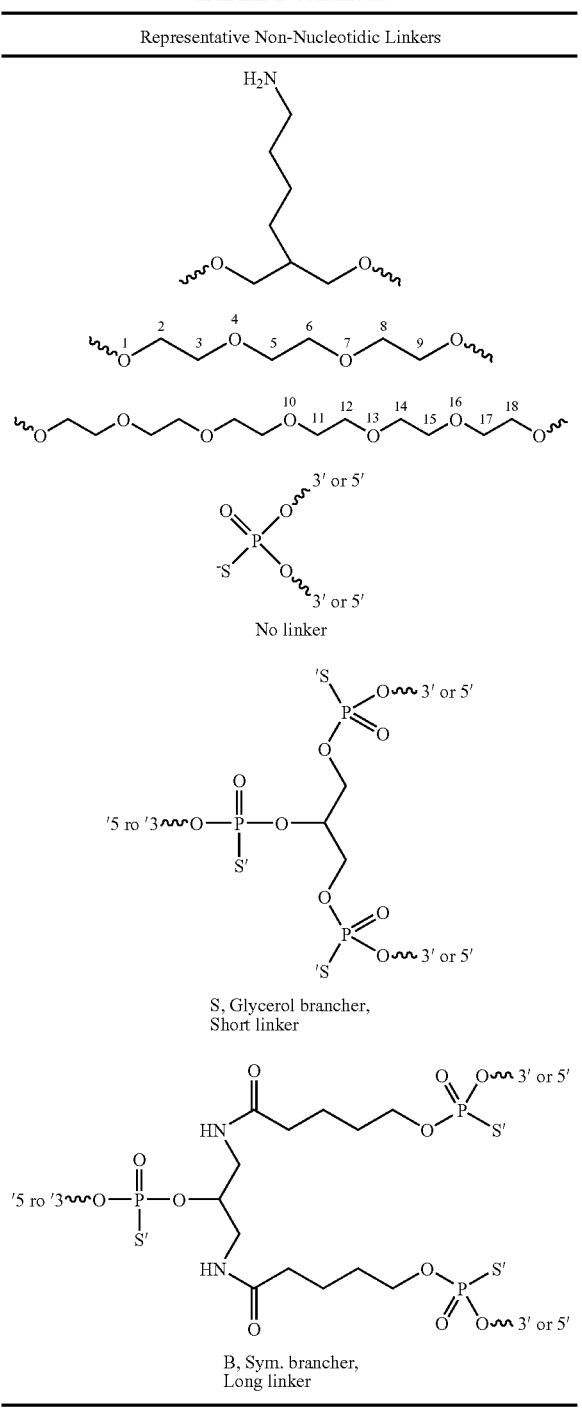

In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4.

Some non-nucleotide linkers according to the invention permit attachment of more than two oligonucleotides. For example, the small molecule linker glycerol has three hydroxyl groups to which oligonucleotides may be covalently attached. Some TLR antagonists according to the invention, therefore, comprise two or more oligonucleotides linked to a nucleotide or a non-nucleotide linker. Such TLR antagonists are referred to as being "branched".

TLR antagonist compounds may comprise at least two oligonucleotides non-covalently linked, such as by electrostatic interactions, hydrophobic interactions, π-stacking interactions, hydrogen bonding and combinations thereof. Non-limiting examples of such non-covalent linkage includes Watson-Crick base pairing, Hoogsteen base pairing and base stacking.

In certain embodiments, pyrimidine nucleosides in the immune regulatory oligonucleotides used in the compositions and methods according to the invention have the structure (II):

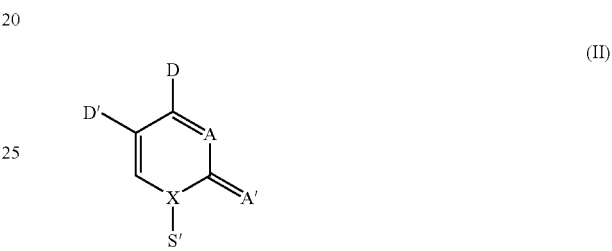

wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In some embodiments hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, (II) is a pyrimidine nucleoside derivative. Examples of pyrimidine nucleoside derivatives include, without limitation, 5-hydroxycytosine, 5-hydroxymethylcytosine, N4-alkylcytosine, or N4-ethylcytosine, araC, 5-OH-dC, N3-Me-dC, and 4-thiouracil. Chemical modified derivatives also include, but are not limited to, thymine or uracil analogues. In some embodiments, the sugar moiety S' in (II) is a sugar derivative. Suitable sugar derivatives include, but are not limited to, trehalose or trehalose derivatives, hexose or hexose derivatives, arabinose or arabinose derivatives.

In some embodiments, the purine nucleosides in the TLR antagonists used in the compositions and methods according to the invention have the structure (III):

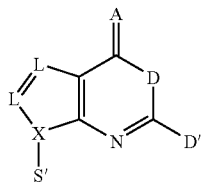

(III)

wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In certain embodiments hydrogen bond donors include, without limitation, —NH—, —NH$_2$, —SH and —OH. In certain embodiments hydrogen bond acceptors include, without limitation, C=O, C=S, —NO$_2$ and the ring nitrogen atoms of an aromatic heterocycle, e.g., N1 of guanine.

In some embodiments, (III) is a purine nucleoside derivative. Examples of purine nucleoside derivatives include, without limitation, guanine analogues such as 7-deaza-G, 7-deaza-dG, ara-G, 6-thio-G, Inosine, Iso-G, loxoribine, TOG(7-thio-8-oxo)-G, 8-bromo-G, 8-hydroxy-G, 5-amino-formycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, 1-(B-D-ribofuranosyl)-2-oxo-7-deaza-8-methyl-purine, 1-(2'-deoxy-β-D-ribofuranosyl)-2-oxo-7-deaza-8-methyl-purine. Chemically modified derivatives also include, but are not limited to, adenine analogues such as 9-benzyl-8-hydroxy-2-(2-methoxyethoxy)adenine, 2-Amino-N2-O-, methyladenosine, 8-Aza-7-deaza-A, 7-deaza-A, Vidarabine, 2-Aminoadenosine, N1-Methyladenosine, 8-Azaadenosine, 5-Iodotubercidin, and N1-Me-dG. In some embodiments, the sugar moiety S' in (III) is a sugar derivative as defined for Formula II.

In certain embodiments of the invention, the TLR antagonist comprises a nucleic acid sequence containing at least one B-L-deoxy nucleoside or 3'-deoxy nucleoside.

In certain embodiments of the invention, the TLR antagonist comprises a nucleic acid sequence containing at least one dinucleotide selected from CpG, C*pG, C*pG* and CpG*, wherein C is cytosine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'- deoxyinosine, or other purine nucleoside analogs, and p is an internucleoside linkage selected from the group consisting of phosphodiester, phosphorothioate, and phosphorodithioate, and wherein the activity of the at least one dinucleotide is regulated by the flanking sequence.

The sequences of selected TLR antagonists within these general structures that would be useful for the present invention include, but are not limited to, those shown in Table 3.

TABLE 3

| SEQ ID NO: | Sequence |
|---|---|
| 5 | 5'-CTATCT<u>GA</u>CGTTCTCTGT-3' |
| 7 | 5'-CTATCT<u>GA</u>CGTTCTCTGT-3' |
| 17 | 5'-CTATCT<u>GA</u>CG$_1$TTCTCTGT-3' |
| 37 | 5'-CTATCT<u>GA</u>CG$_4$TTCTCTGT-3' |
| 39 | 5'-CTATCT<u>GA</u>C$_4$GTTCTCTGT-3' |
| 41 | 5'-CTATCT<u>GA</u>C$_5$GTTCTCTGT-3' |
| 43 | 5'-CTATCT<u>GA</u>C$_6$GTTCTCTGT-3' |
| 45 | 5'-CTATCT<u>GA</u>CG$_5$TTCTCTGT-3' |
| 47 | 5'-CTATCT<u>GA</u>C$_7$GTTCTCTGT-3' |
| 64 | 5'-CTATCT<u>AA</u>CGTTCTCTGT-3' |
| 67 | 5'-CTATCT<u>AA</u>CG$_1$TTCTCTGT-3' |
| 22 | 5'-CTATCTGAmCGTTCTCTGT-3' |
| 9 | 5'-CTATCT<u>GU</u>CGTTCTCTGT-3' |
| 10 | 5'-CTATCT<u>GU</u>CGTTCTCTGT-3' |
| 19 | 5'-CTATCT<u>GU</u>CG$_1$TTCTCTGT-3' |
| 38 | 5'-CTATCT<u>GU</u>CG$_4$TTCTCTGT-3' |
| 40 | 5'-CTATCT<u>GU</u>C$_4$GTTCTCTGT-3' |
| 42 | 5'-CTATCT<u>GU</u>C$_5$GTTCTCTGT-3' |
| 44 | 5'-CTATCT<u>GU</u>C$_6$GTTCTCTGT-3' |
| 46 | 5'-CTATCT<u>GU</u>CG$_5$TTCTCTGT-3' |
| 48 | 5'-CTATCT<u>GU</u>C$_7$GTTCTCTGT-3' |
| 66 | 5'-CTATCT<u>AU</u>CGTTCTCTGT-3' |
| 69 | 5'-CTATCT<u>AU</u>CG$_1$TTCTCTGT-3' |
| 65 | 5'-CTATCT<u>AG</u>CGTTCTCTGT-3' |
| 68 | 5'-CTATCT<u>AG</u>CG$_1$TTCTCTGT-3' |
| 23 | 5'-CTATCTGmACGTTCTCTGT-3' |
| 24 | 5'-CTATCTGmAmCGTTCTCTGT-3' |
| 25 | 5'-CTATCTGAC$_2$GTTCTCTGT-3' |
| 27 | 5'-CTATCTGTC$_2$GTTCTCTGT-3' |
| 33 | 5'-CTATCTGAC$_3$GTTCTCTGT-3' |
| 35 | 5'-CTATCTGTC$_3$GTTCTCTGT-3' |
| 26 | 5'-CTATCTGACG$_2$TTCTCTGT-3' |
| 28 | 5'-CTATCTGTCG$_2$TTCTCTGT-3' |
| 34 | 5'-CTATCTGACG$_3$TTCTCTGT-3' |

TABLE 3-continued

| SEQ ID NO: | Sequence |
|---|---|
| 36 | 5'-CTATCTGTCG$_3$TTCTCTGT-3' |
| 21 | 3'-TCTTGCAGTCT-X$_2$-TCTGACGTTCT-3' |
| 52 | 5'-CCTACTAGCGTX$_1$CTCATC-3' |
| 53 | 5'-CCTACTAGCGX$_1$TCTCATC-3' |
| 54 | 5'-CCTACTAG$_3$CGTTCTCATC-3' |
| 55 | 5'-TCCATGA$_1$CGTTCCTGATGC-3' |
| 56 | 5'-CTATCTGAC$_2$G$_2$TTCTCTGT-3' |
| 57 | 5'-C$_2$T$_2$A$_2$T$_2$C$_2$T$_2$G$_2$A$_2$C$_2$G$_2$T$_2$T$_2$C$_2$T$_2$C$_2$T$_2$G$_2$T$_2$-3' |
| 29 | 5'-CTATCTGAX$_1$GTTCTCTGT-3' |
| 30 | 5'-CTATCTGACX$_1$TTCTCTGT-3' |
| 31 | 5'-CTATCTGTX$_1$GTTCTCTGT-3' |
| 32 | 5'-CTATCTGTCX$_1$TTCTCTGT-3' |
| 61 | 5'-CTATCTAGCGTX$_1$CTCTGT-3' |
| 62 | 5'-CTATCTAGCGX$_1$TCTCTGT-3' |
| 63 | 5'-CTATCTAGCGX$_1$X$_1$CTCTGT-3' |
| 58 | 5'-CTATCTGACGTX$_3$CTCTGT-3' |
| 59 | 5'-CTATCTGACGX$_3$TCTCTGT-3' |
| 60 | 5'-CTATCTGACGX$_3$X$_3$CTCTGT-3' |
| 70 | 5'-CTATCTAGCGTX$_3$CTCTGT-3' |
| 71 | 5'-CTATCTAGCGX$_3$TCTCTGT-3' |
| 72 | 5'-CTATCTAGCGX$_3$X$_3$CTCTGT-3' |
| 74 | 5'-CTATCT$\underline{GA}$CGTTCTCTGT-3' |
| 76 | 5'-CCTACTAG$_6$CGTTCTCATC-3' |
| 77 | 5'-TCCATGACGU$_1$TCCTGATGC-3' |
| 78 | 5'-CTATCTGX$_2$CGTTCTCTGT-3' |
| 79 | 5'-CTATCTX$_2$ACGTTCTCTGT-3' |
| 80 | 5'-CTATCTU$_2$ACGTTCTCTGT-3' |
| 81 | 5'-CTATCTGU$_2$CGTTCTCTGT-3' |
| 82 | 5'-CTATCTGACGX$_2$TCTCTGT-3' |
| 83 | 5'-CTATCTGACGTX$_2$CTCTGT-3' |
| 84 | 5'-CTATCTGX$_3$CGTTCTCTGT-3' |
| 85 | 5'-CTATCTX$_3$ACGTTCTCTGT-3' |
| 86 | (5'-TCT$\underline{GA}$CGTTCT)$_2$X$_2$ |
| 87 | (5'-TCT$\underline{GA}$CG$_1$TTCT)$_2$X$_2$ |
| 88 | (5'-TCT$\underline{GA}$CG$_4$TTCT)$_2$X$_2$ |
| 89 | (5'-TCTCT$\underline{GA}$CGTT)$_2$X$_2$ |
| 90 | 5'-TCT$\underline{GA}$CG$_1$TTCT-X$_3$-TGACCGGTCA-3' |
| 93 | (5'-TCT$\underline{GU}$CGTTCT)$_2$X$_2$ |
| 94 | (5'-TCT$\underline{GU}$CG$_1$TTCT)$_2$X$_2$ |
| 93 | (5'-TCT$\underline{GA}$CG$_4$TTCT)X$_2$ |
| 96 | (5'-TCT$\underline{GA}$CG$_1$TT)$_2$X$_2$ |
| 95 | 5'-TCT$\underline{GA}$CG$_1$TTCT-X$_3$-TCAACCACACA-3' |
| 98 | 5'-CTATCT$\underline{GA}$CG$_1$TTCT$\underline{CU}$G$\underline{U}$-3' |
| 99 | 5'-CTATCT$\underline{GU}$CG$_1$TTCT$\underline{CU}$G$\underline{U}$-3' |
| 100 | (5'-$\underline{UGU}$CG$_1$TTCT)X$_2$ |
| 101 | (5'-$\underline{UGA}$CG$_1$TTCT)$_2$X$_2$ |
| 102 | 5'-CTATCTGAC$^1$GTTCTCTGT-3' |
| 103 | 5'-CTATCTGAC$^2$GTTCTCTGT-3' |
| 104 | 5'-CTATCTGAC$^3$GTTCTCTGT-3' |
| 105 | 5'-CTATCTGAC$^2$G$^1$TTCTCTGT-3' |

Underlined G, A or U=2'-OMe; Underlined T=3'-OMe; A$_1$=3'-OMe; G$_1$=7-deaza-dG; m=P-Me; A$_2$, T$_2$, C$_2$, and G$_2$=B-L-deoxy nucleoside; X$_1$=abasic; X$_2$=glycerol linker, X$_3$=C3-linker; C$_3$ and G$_3$=3'-deoxy-nucleoside; G$_4$=araG; C$_4$=araC; C$_5$=5-OH-dC; C$_6$=1-(2'-deoxy-β-D-ribofuranosyl)-2-oxo-7-deaza-8-methyl-purine; G$_5$=N1-Me-dG; C$_7$=N3-Me-dC; U$_1$=3'-OMe; U$_2$=dU; C$^1$=2'-O-methyl-C; C$^2$=5-methyl-dC; C$^3$=2'-O-methyl-5-methyl-C; G$^1$=2'-O-methyl-G In some embodiments, the TLR antagonists each have from about 6 to about 35 nucleoside residues, preferably from about 9 to about 30 nucleoside residues, more preferably from about 11 to about 23 nucleoside residues. In some embodiments, the TLR antagonists have from about 6 to about 18 nucleoside residues.

In a second aspect, the invention provides a method for therapeutically treating a disease associated with high blood lipid concentration and/or high blood cholesterol concentration in a mammal, such method comprising inhibiting TLR signaling in the mammal, as described in the first aspect of the invention. In some embodiments, TLR signaling is inhibited by administering to the mammal one or more TLR antagonist compounds according to the invention in a pharmaceutically effective amount. In some embodiments TLR signaling is inhibited by inhibiting the expression of one or more TLR, or another protein in the TLR signaling pathway. In certain preferred embodiments of this aspect of the invention, the disease is hypercholesterolemia, hyperlipidemia, coronary heart disease, arteriosclerosis, atherosclerosis, stroke, peripheral vascular disease, diabetes or high blood pressure.

In a third aspect, the invention provides a method for preventing a disease associated with high blood lipid concentration and/or blood cholesterol concentration in a mammal having elevated blood cholesterol and/or blood lipid, such method comprising inhibiting TLR signaling in the mammal as described in the first aspect of the invention. In some embodiments, TLR signaling is inhibited by administering to the mammal one or more TLR antagonist compounds according to the invention in a pharmaceutically effective amount. In some embodiments TLR signaling is inhibited by inhibiting the expression of one or more TLR, or another protein in the TLR signaling pathway. In certain preferred embodiments, the disease is hypercholesterolemia, hyperlipidemia, coronary heart disease, arteriosclerosis, atherosclerosis, stroke, peripheral vascular disease, diabetes or high blood pressure.

In some embodiments, the methods according to the invention further comprise administering to the mammal one or more cholesterol lowering compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof.

In the methods according to the invention, administration of the TLR antagonist compound can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of the TLR antagonist compound can be carried out using known procedures at dosages and for periods of time effective to reduce symptoms or surrogate markers of the disease. When administered systemically, the therapeutic composition is preferably administered at a sufficient dosage to attain a blood level of the TLR antagonist compound from about 0.0001 micromolar to about 10 micromolar. For localized administration, much lower concentrations than this may be effective, and much higher concentrations may be tolerated. In some preferred embodiments, a total dosage of the TLR antagonist compound ranges from about 0.001 mg per patient per day to about 200 mg per kg body weight per day. It may be desirable to administer simultaneously, or sequentially a therapeutically effective amount of one or more of the TLR antagonists to an individual as a single treatment episode.

The TLR antagonist compound may be administered or used in combination with other compounds including, without limitation, one or more lipid lowering compounds or compositions, cholesterol lowering compounds or compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof.

The methods according to the invention are useful for the prophylactic or therapeutic treatment of human and/or animal disease. For example, the methods may be useful for adult, pediatric and veterinary applications.

In any of the methods according to the invention, the TLR antagonist compound can be administered in combination with any other agent useful for treating the disease or condition that does not diminish the antagonist activity of the TLR antagonist compound. In any of the methods according to the invention, the agent useful for treating the disease or condition includes, but is not limited to, one or more lipid lowering compounds or compositions, cholesterol lowering compounds or compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof, which can enhance the specificity or magnitude of the response to the TLR antagonist. For example, in the treatment of hyperlipidemia and/or hypercholesterolemia, it is contemplated that the TLR antagonist compound may be administered in combination with one or more lipid and/or cholesterol lowering compounds, including, without limitation, statins, targeted therapeutic agents and/or monoclonal antibodies.

The following examples are intended to further illustrate certain exemplary embodiments of the invention and are not intended to limit the scope of the invention. For example, representative TLR antagonists are shown in the following examples, but do not limit the scope of TLRs to which the antagonist of the invention are applicable.

The patents and publications cited herein represent common knowledge in the field and are incorporated by reference in their entirety. Any conflict between the teachings of the cited references and the instant specification shall be resolved in favor of the latter.

Example 1

Synthesis of Oligonucleotides Containing Immune Regulatory Moieties

All synthetic oligonucleotides were synthesized according to standard procedures (see, e.g., U.S. Patent Publication No. 2004/0097719).

Oligonucleotides were synthesized on a 1 µM scale using an automated DNA synthesizer (Expedite 8909; PerSeptive Biosystems, Framingham, Mass.), following standard linear synthesis or parallel synthesis procedures (see, e.g., FIGS. 5 and 6 of U.S. Patent Publication No. 2004/0097719).

Deoxyribonucleoside phosphoramidites were obtained from (Aldrich-Sigma, St Louis, Mo.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). β-L-2'-deoxyribonucleoside phosphoramidite, alpha-2'-deoxyribonucleoside phosphoramidite, mono-DMT-glycerol phosphoramidite and di-DMT-glycerol phosphoramidite were obtained from ChemGenes (Willmington, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Idera Pharmaceuticals, Inc. (Cambridge, Mass.) (Noronha et al. (2000) *Biochem.* 39:7050-7062).

All nucleoside phosphoramidites were characterized by $^{31}$P and $^1$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Cholesterol and Lipid Lowering Activities of TLR Antagonists In vivo

Female C57BL/6 mice of 5 weeks age were obtained from The Jackson Laboratory. All animal experiments were performed as per guidelines of Idera Pharmaceuticals ICAUC approved protocols. Mice were fed a Western diet consisting of 60% lard (Research Diets, New Brunswick, N.J.). TLR antagonist was administered to mice at doses of 5 and 20 mg/kg, s.c two times a week for five weeks starting at week 6 to week 10. Lipitor® was administered to mice at a dose of 20 mg/kg i.g five times a week for five weeks. Control group of mice were injected with PBS. Each group had five mice. Blood was collected during the course of the study and at week 12 when the experiment was terminated. The level of serum cholesterol was determined in each sample by "Enzy-Chrom™ Cholesterol Assay Kit" from BioAssay System.

Example 3

Cholesterol, Lipoprotein, Lipid and Glucose Lowering Activities of TLR Antagonists In vivo Female C57BL/6 or ApoE-deficient mice of 5 weeks old were obtained from The Jackson Laboratory. All animal experiments were performed as per guidelines of Idera Pharmaceuticals ICAUC approved protocols. Mice were fed a Western diet consisting of 60% lard (Research Diets, New Brunswick, N.J.). Antagonist was administered to mice at doses of 15 mg/kg, s.c two times a week for five weeks starting at week 6 to week 10. Control group of mice were injected with PBS. Each group had 15 mice. Blood was collected every week after overnight fasting of mice until at week 12 when the experiment was terminated and serum levels of cholesterol, HDL, LDL, ALT, AST, triglyceride and glucose were determined at Quest Laboratories.

Example 4

Body Weight Lowering Activities of TLR Antagonists In vivo

Female C57BL/6 or ApoE-deficient mice of 5 weeks old were obtained from The Jackson Laboratory. All animal experiments were performed as per guidelines of Idera Pharmaceuticals ICAUC approved protocols. Mice were fed a Western diet consisting of 60% lard (Research Diets, New Brunswick, N.J.). Antagonist was administered to mice at doses of 15 mg/kg, s.c two times a week for five weeks starting at week 6 to week 10. Control group of mice were injected with PBS. Each group had 15 mice. Body weight was measured.

What is claimed is

1. A method for lowering blood concentrations of cholesterol, lipids and/or low density lipoprotein in a mammal having elevated concentrations thereof, the method comprising administering to the mammal an inhibitor of the activity of TLR7, TLR8 and/or TLR9.

2. The method according to claim 1, wherein the inhibitor is a compound selected from the group consisting of a small molecule; an antibody; a cyclohexene derivative; a lipid derivative; a synthetic oligonucleotide comprising a "CCT" triplet and a "GGG" triplet; a synthetic oligonucleotide comprising regions containing "OGG" and/or "GGGG" and/or "GC" sequences; a synthetic oligonucleotide that is methylated; a synthetic, immune inhibitory oligonucleotide, having one or more chemical modifications in the sequence flanking an immune stimulatory motif that would be immune stimulatory but for the modification; and a synthetic immune inhibitory oligonucleotide, containing a modified immune stimulatory motif comprising one or more modified immune stimulatory motifs, wherein the modified immune stimulatory motif would be immune stimulatory but for the modification.

3. The method according to claim 2, wherein the small molecule is chloroquine or hydroxychloroquine.

4. The method according to claim 1, wherein the inhibitor is a TLR7,TLR8 and/or TLR9 antagonist compound having the structure

wherein:
CG is an oligonucleotide motif, wherein C is cytosine or a pyrimidine nucleotide derivative, and
G is guanosine or a purine nucleotide derivative;
$N_1$ is a modified nucleotide that suppresses the activity of the oligonucleotide motif;
$N_2$-$N_3$, at each occurrence, is independently a nucleotide, nucleotide derivative or modified nucleotide that suppresses the activity of the oligonucleotide motif;
$N^1$-$N^3$, at each occurrence, is independently a nucleotide or nucleotide derivative;
$N^m$ and $N_m$, at each occurrence, is independently a nucleotide, nucleotide derivative or non-nucleotide linkage;
wherein the oligonucleotide contains less than 3 consecutive guanosine nucleotides;
wherein the oligonucleotide motif would be immunostimulatory but for the one or more modified nucleotide that suppresses the activity of the oligonucleotide motif;
and wherein m is an integer from 0 to about 30.

5. The method according to claim 1, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

6. The method according to claim 1, further comprising administering to the mammal one or more lipid lowering compounds or compositions, cholesterol lowering compounds or compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof.

7. The method according to claim 6, wherein the cholesterol lowering composition is a statin.

8. A method for therapeutically treating a mammal having a hypercholesterolemia and/or hyperlipidemia, the method comprising administering to the mammal an inhibitor of the activity of TLR7, TLR8 and/or TLR9.

9. The method according to claim 8, wherein the inhibitor is a compound selected from the group consisting of a small molecule; an antibody; a cyclohexene derivative; a lipid derivative; a synthetic oligonucleotide comprising a "CCT" triplet and a "GGG" triplet; a synthetic oligonucleotide comprising regions containing "GGG" and/or "GGGG" and/or "GC" sequences; a synthetic oligonueleotide that is methylated or a synthetic;

immune inhibitory oligonucleotides, having one or more chemical modifications in the sequence flanking an immune stimulatory motif that would be immune stimulatory but for the modification; and a synthetic immune inhibitory oligonucleotide, containing a modified immune stimulatory motif comprising one or more modified immune stimulatory motifs, wherein the modified immune stimulatory motif would be immune stimulatory but for the modification.

10. The method. according to claim 9, wherein the small molecule is chloroquine or hydroxychloroquine.

11. The method according to claim 8, wherein the inhibitor is a TLR7, TLR8 and/or TLR9 antagonist compound having the structure

wherein:
CG is an oligonucleotide motif, wherein C is cytosine or a pyrimidine nucleotide derivative, and
G is guanosine or a purine nucleotide derivative;
$N_1$ is a modified nucleotide that suppresses the activity of the oligonucleotide motif;
$N_2$-$N_3$, at each occurrence, is independently a nucleotide, nucleotide derivative or modified nucleotide that suppresses the activity of the oligonucleotide motif;
$N^1$-$N^3$, at each occurrence, is independently a nucleotide or nucleotide derivative;
$N^m$ and $N_m$, at each occurrence, is independently a nucleotide, nucleotide derivative or non-nucleotide linkage;
wherein the oligonucleotide contains less than 3 consecutive guanosine nucleotides;

wherein the oligonucleotide motif would be immunostimulatory but for the one or more modified nucleotide that suppresses the activity of the oligonucleotide motif; and wherein m is an integer from 0 to about 30.

12. The method according to claim 8, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

13. The method according to claim 8, further comprising administering to the mammal one or more lipid lowering compounds or compositions, cholesterol lowering compounds or compositions, diuretics, non-steroidal anti-inflammatory compounds (NSAIDs), statins, antibodies, antisense oligonucleotides, TLR agonists, TLR antagonists, peptides, proteins or gene therapy vectors or combinations thereof.

14. The method according to claim 13, wherein the cholesterol lowering composition is a statin.

15. A method for preventing hypercholesterolemia and/or hyperlipidemia in a mammal the method comprising administering to the mammal an inhibitor of the activity of TLR7, TLR8 and/or TLR9.

16. The method according to claim 15, wherein the inhibitor is a compound selected from the group consisting of a small molecule; an antibody; a cyclohexene derivative; a lipid derivative; a synthetic oligonucleotide comprising a "CCT" triplet and a "GGG" triplet; a synthetic oligonucleotide comprising regions containing "GGG" and/or "GGGG" and/or "GC" sequences; a synthetic oligonucleotide that is methylated or a synthetic, immune inhibitory oligonucleotides, having one or more chemical modifications in the sequence flanking an immune stimulatory motif that would be immune stimulatory but for the modification; and a synthetic immune inhibitory oligonucleotide, containing a modified immune stimulatory motif comprising one or more modified immune stimulatory motifs, wherein the modified immune stimulatory motif would be immune stimulatory but for the modification.

17. The method according to claim 16, wherein the small molecule is chloroquine or hydroxychloroquine.

18. The method according to claim 15, wherein the inhibitor is a TLR7, TLR8 and/or TLR9 antagonist compound having the structure

wherein:
CG is an oligonucleotide motif, wherein C is cytosine or a pyrimidine nucleotide derivative, and
G is guanosine or a purine nucleotide derivative;
$N_1$ is a modified nucleotide that suppresses the activity of the oligonucleotide motif, $N_2$-$N_3$, at each occurrence, is independently a nucleotide, nucleotide derivative or modified nucleotide that suppresses the activity of the oligonucleotide motif;
$N^1$-$N^3$, at each occurrence, is independently a nucleotide or nucleotide derivative;
$N^m$ and $N_m$, at each occurrence, is independently a nucleotide, nucleotide derivative or non-nucleotide linkage;
wherein the oligonucleotide contains less than 3 consecutive guanosine nucleotides;
wherein the oligonucleotide motif would be immunostimulatory but for the one or more modified nucleotide that suppresses the activity of the oligonucleotide motif; and wherein m is an integer from 0 to about 30.

19. The method according to claim 15, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

20. The method according to claim 15, further comprising administering to the mammal one or more lipid lowering compounds or compositions, cholesterol lowering compounds or compositions, diuretics, nonsteroidal anti-inflammatory compounds (NSAIDs), statins, antibodies, antisense oligonucleotides, TLR agonists, TLR antagonists, peptides, proteins or gene therapy vectors or combinations thereof.

21. The method according to claim 20, wherein the cholesterol lowering composition is a statin.

22. The method according to claim 4, wherein the modified nucleotide that suppresses the activity of the oligonucleotide motif is a 2'-substituted nucleotide or a 3'-substituted nucleotide.

23. The method according to claim 4, wherein the inhibitor comprises two compounds linked by a non-nucleotide linker at their 3' ends or by a functionalized sugar or by a functionalized nucleobase via a non-nucleotide linker.

24. The method according to claim 23, wherein the non-nucleotide linker linking the two compounds is glycerol (1,2,3-Propanetriol), 1,2,4, Butanetriol, 2-(hydroxymethyl)- 1,3-propanediol, 2-(hydroxymethyl) 1,4-butanediol, 1,3,5-Pentanetriol, 1,1,1-Tris(hydroxymethyl)ethane, 1,1,1-Tris (hydroxymethy)nitromethane, 1,1,1-Tris(hydroxymethyl) propane, 1,2,6-Hexanetriol, 3-Methyl-1,3,5 -pentanetriol, 1,2,3-Heptanetriol, 2-Amino-2-(hydroxymethyl)-1,3-propanediol, N- [Tris(hydroxymethyl) methyl]acrylamide, cis-1,3,5-Cyclohexanetriol, Cis-1,3,5-Tri(hydroxymethyl)cyclohexane, 3,5-Di(hydroxymethyl)phenol, 1,3,5-Trihydroxyl-benzene, 3,5-Di(hydroxymethyl)benzene, 1,3-Di(hydroxyethoxy)-2-hydroxyl-propane, 1,3-Di (hydroxypropoxy)-2-hydroxyl-propane, 2-Deoxy-D-ribose, 1,2,4-Trihydroxyl-benzene, D- Galactoal, 1,6-anhydro-β-D-Glucose, 1,3,5-Tris(2-hydroxyethyl)-Cyanuric acid, Gallic acid, 3,5,7-Trihydroxyflavone, 4,6-Nitropyrogallol, Ethylene glycol, 1,3-Propanediol, 1,2-Propanediol, 1,4-Butanediol, 1,3-Butanediol, 2,3-Butanediol, 1,4-Butanediol, 1,5-Pentanediol, 2,4-Pentanediol, 1,6-Hexanediol, 1,2-Hexanediol, 1,5-Hexanediol, 2,5-Hexanediol, 1,7-Heptanediol, 1,8-Octanedial, 1,2-Octanediol, 1,9-Nonanediol, 1,12-Dodecanediol, Triethylene glycol, Tetraethylene glycol, 2-(1-Aminopropyl)-1,3-propanediol, or 1,2-Dideoxyribose.

25. The method according to claim 24, wherein the non-nucleotide linker linking the two compounds is glycerol.

26. The method according to claim 4, wherein the pyrimidine derivative is 2'-deoxythymidine, 1-(2'-deoxy-β-D-ribofuranosyl)-2-oxo-7-deaza-8-methyl-purine, 2'-dideoxy-5-halocytosine, 2-dideoxy-5-nitrocytosine, arabinocytidine, 2'-deoxy-5-hydroxycyidine, 2-deoxy-N4-alkyl-cytidine, 2'-deoxy4-thiouridine, or other pyrimidine nucleoside analogs.

27. The method according to claim 4, wherein the purine derivative is 2-deoxy-7-deazaguanosine, 2'-deoxy-6-thioguanosine, arabinoguanosine, 2'-deoxyinosine, or other purine nucleoside analogs.

28. The method according to claim 11, wherein the modified nucleotide that suppresses the activity of the oligonucleotide motif is a 2'-substituted nucleotide or a 3'-substituted nucleotide.

29. The method according to claim 11, wherein the inhibitor comprises two compounds linked by a non-nucleotide linker at their 3' ends or by a functionalized sugar or by a functionalized nucleobase via a non-nucleotide linker.

30. The method according to claim 29, wherein the non-nucleotide linker linking the two compounds is glycerol (1,2,3-Propanetriol), 1,2,4, Butanetriol, 2-(hydroxymethyl)-1,3- propanediol, 2-(hydroxymethyl)1,4-butanediol, 1,3,5-Pentanetriol, 1,1,1-Tris(hydroxymethyDethane, 1,1,1-Tris(hydroxymethyl)nitromethane, 1,1,1-Tris(hydroxymethyl)propane, 1,2,6-Hexanetriol, 3-Methyl-1,3,5-pentanetriol, 1,2,3-Heptanetriol, 2-Amino-2-(hydroxymethyl)-1,3-propanediol, N-[Tris(hydroxymethy)methyl]acrylamide, cis-1,3,5-Cyclohexanetriol, Cis-1,3,-Tri(hydroxymethyl)cyclohexane, 3,5-Di(hydroxymethyl)phenol, 1,3,5-Trihydroxyl-benzene, 3,5-Di(hydroxymethyl)benzene, 1,3-Di(hydroxyethoxy)-2-hydroxyl-propane, 1,3-Di(hydroxypropoxy)-2-hydroxyl-propane, 2-Deoxy-D-ribose, 1,2,4-Trihydroxyl-benzene, D-Galactoal, 1,6-anhydro-β-D-Glucose, 1,3,5-Tris(2-hydroxyethyl)-Cyanuric acid, Gallic acid, 3,5,7-Trihydroxyflavone, 4,6-Nitropyrogallol, Ethylene glycol, 1,3-Propanediol, 1,2-Propanediol, 1,4-Butanediol, 1,3-Butanediol, 2,3-Butanediol, 1,4-Butanediol, 1,5-Pentanediol, 2,4-Pentanediol, 1,6-Hexanediol, 1,2-Hexanediol, 1,5-Hexanediol, 2,5-Hexanediol, 1,7-Heptanediol, 1,8-Octanediol, 1,2-Octanediol, 1,9-Nonanediol, 1,12-Didecanediol, Triethylene glycol, Tetraethylene glycol, 2-(1-Aminopropyl)-1,3-propanediol, or 1,2-Dideoxyribose.

31. The method according to claim 30, wherein the non-nucleotide linker linking the two compounds is glycerol.

32. The method according to claim 11, wherein the pyrimidine derivative is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-5-hydroxycytidine, 2'-deoxy-N4-alkyl-cytidine, 2-deoxy-4-thiouridine, or other pyrimidine nucleoside analogs.

33. The method according to claim 11, wherein the purine derivative is 2'-deoxy-7-deazaguanosine, 2'-deoxy-6-thioguanosine, arabinoguanosine, 2'-deeoxyinosine, or other purine nucleoside analogs.

34. The method according to claim 18, wherein the modified nucleotide that suppresses the activity of the oligonucleotide motif is a 2'-substituted nucleotide or a 3'-substituted nucleotide.

35. The method according to claim 18, wherein the inhibitor comprises two compounds linked by a non-nucleotide linker at their 3' ends or by a functionalized sugar or by a funetionalized nucleobase via a non-nucleotide linker.

36. The method according to claim 35, wherein the non-nucleotide linker linking the two compounds is glycerol (1,2,3-Propanetriol), 1,2,4, Butanetriol, 2-(hydroxymethyl)-1,3-propanediol, 2-(hydroxymethyl)1,-butanediol, 1,3,5-Pentanetriol, 1,1,1-Tris(hydroxymethyl)ethane, 1,1,1-Tris(hydroxymethyl)nitromethane, 1,1,1-Tris(hydroxymethyl)propane, 1,2,6-Hexanetriol, 3-Methyl-1,3,5-pentanetriol, 1,2,3-Heptanetriol, 2-Amino-2-(hydroxymethyl)-1,3-propanediol, N-[Tris(hydroxymethyl)methyl ]acrylamide, cis-13,5-Cyclohexanetriol, Cis-1,3,5-Tri(hydroxymethyl)cyclohexane, 3,5-Di(hydroxymethyl)phenol, 1,3,5-Trihydroxyl-benzene, 3,5-Di(hydroxymethyl)benzene, 1,3-Di(hydroxyethoxy)-2-hydroxyl-propane, 1,3-Di(hydroxypropoxy)-2-hydroxyl-propane, 2-Deoxy-D-ribose, 1,2,4-Trihydroxyl-benzene, D-Galactoa, 1,6-anhydro-β-D-Glucose, 1,3,5-Tris(2-hydroxyethyl)-Cyanuric acid, Gallic acid, 3,5,-Trihydroxyflavone, 4,6-Nitropyrogallol, Ethylene glycol, 1,3-Propanediol, 1,2-Propanediol, 1,4-Butanedial, 1,3-Butanediol, 2,3-Butanediol, 1,4-Butanediol, 1,5-Pentanediol, 2,4-Pentanediol, 1,6-Hexanedio 1,1,2-Hexanediol, 1,5-Hexanediol, 2,5-Hexanediol, 1,7-Heptanediol, 1,8-Octanediol, 1,2-Octanediol, 1,9-Nonanediol, 1,12-Dodecanediol, Triethylene glycol, Tetraethylene glycol, 2-(1-Aminopropyl)-1,3-propanediol, or 1,2-Dideoxyribose.

37. The method according to claim 36, wherein the non-nucleotide linker linking the two compounds is glycerol.

38. The method according to claim 18, wherein the pyrimidine derivative is 2'-deoxythymidine, 1-(2'-deoxy-β-D-ribofuranosyl)-2-oxo-7-deaza-8-methyl-purine, 2'-dideoxy-5-haiocytosine, 2'-dideoxy-5-nitrocytosine, arabinocytidine, 2'-deoxy-5-hydroxycytidine, 2'-deoxy-N4-alkyl-cytidine, 2'-deoxy-4-thiouridine, or other pyrimidine nucleoside analogs.

39. The method according to claim 18, wherein the purine derivative is 2'-deoxy-7-deazaguanosine, '-deoxy-6-thioguanosine, arabinoguanosine, 2'-deoxyinosine, or other purine nucleoside analogs.

40. The method according to claim 22, wherein the 2'-substituted nucleotide is a 2-O-methyl nucleotide.

41. The method according to claim 28, wherein the 2'-substituted nucleotide is a 2-O-methyl nucleotide.

42. The method according to claim 34, wherein the 2'-substituted nucleotide is a 2-O-methyl nucleotide.

* * * * *

```
                        SEQUENCE LISTING

<160> NUMBER OF SEQ ID NOS: 101

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctatctgacg ttctctgt                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctatctgtcg ttctctgt                                                 18

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-G

<400> SEQUENCE: 3
tctgacnttc t                                                        11

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
```
ctatctcacc ttctctgt                                                          18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 5
ctatctgacg ttctctgt                                                          18

<210> SEQ ID NO 6
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: 2'-OMe

<400> SEQUENCE: 6
ctatctgacg uuctctgt                                                          18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 2'-OMe

<400> SEQUENCE: 7
ctatctgacg ttctctgt                                                          18

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgaccggtca                                                                   10

<210> SEQ ID NO 9
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 2'-OMe

<400> SEQUENCE: 9
ctatctgucg ttctctgt                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 10
ctatctgucg ttctctgt                                                    18

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcaaccacac a                                                           11

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcctggcggg gaagt                                                       15

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000
```

```
<210> SEQ ID NO 16

<400> SEQUENCE: 16

000

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 17
ctatctgacn ttctctgt                                                    18

<210> SEQ ID NO 18

<400> SEQUENCE: 18

000

<210> SEQ ID NO 19
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 19
ctatctgucn ttctctgt                                                    18

<210> SEQ ID NO 20

<400> SEQUENCE: 20

000

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctgacgttc t                                                           11
```

-continued

```
<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgttctctgt                                                          10

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acgttctctg t                                                        11

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgttctctgt                                                          10

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: B-L-deoxy nucleoside-C

<400> SEQUENCE: 25
ctatctgang ttctctgt                                                 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: B-L-deoxy nucleoside-G

<400> SEQUENCE: 26
ctatctgacn ttctctgt                                                 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
                                 oligonucleotide
<220> FEATURE:
<221> NAME/KEY: modified_base
<222> LOCATION: (9)
<223> OTHER INFORMATION: B-L-deoxy nucleoside-C

<400> SEQUENCE: 27
ctatctgtng ttctctgt                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: B-L-deoxy nucleoside-G

<400> SEQUENCE: 28
ctatctgtcn ttctctgt                                                 18

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 ctatctga                                                             8

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 ctatctgac                                                            9

<210> SEQ ID NO 31
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 ctatctgt                                                             8

<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 ctatctgtc                                                            9
```

```
<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 3'-deoxy-nucleoside-C

<400> SEQUENCE: 33
ctatctgang ttctctgt                                                   18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-deoxy-nucleoside-G

<400> SEQUENCE: 34
ctatctgacn ttctctgt                                                   18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 3'-deoxy-nucleoside-C

<400> SEQUENCE: 35
ctatctgtng ttctctgt                                                   18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-deoxy-nucleoside-G

<400> SEQUENCE: 36
ctatctgtcn ttctctgt                                                   18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
```

```
<223> OTHER INFORMATION: 2'-OMe
<220> FEATURE:
<221> NAME/KEY: modified_base
<222> LOCATION: (10)
<223> OTHER INFORMATION: araG

<400> SEQUENCE: 37
ctatctgacn ttctctgt                                                      18

<210> SEQ ID NO 38
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: araG

<400> SEQUENCE: 38
ctatctgucn ttctctgt                                                      18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: araC

<400> SEQUENCE: 39
ctatctgang ttctctgt                                                      18

<210> SEQ ID NO 40
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: araC

<400> SEQUENCE: 40
ctatctgung ttctctgt                                                      18
```

```
<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 5-OH-dC

<400> SEQUENCE: 41
ctatctgang ttctctgt                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 5-OH-dC

<400> SEQUENCE: 42
ctatctgung ttctctgt                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methyl-purine-C

<400> SEQUENCE: 43
ctatctgang ttctctgt                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methyl-purine-C

<400> SEQUENCE: 44
ctatctgung ttctctgt                                                    18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: N1-Me-dG

<400> SEQUENCE: 45
ctatctgacn ttctctgt                                                    18

<210> SEQ ID NO 46
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: N1-Me-dG

<400> SEQUENCE: 46
ctatctgucn ttctctgt                                                    18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: N3-Me-dC

<400> SEQUENCE: 47
ctatctgang ttctctgt                                                    18
```

```
<210> SEQ ID NO 48
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: N3-Me-dC

<400> SEQUENCE: 48
ctatctgung ttctctgt                                                     18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)
<223> OTHER INFORMATION: 2'-OMe

<400> SEQUENCE: 49
ctatctagcg ttctctgt                                                     18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: 2'-OMe

<400> SEQUENCE: 50
ctatctagcg ttctctgt                                                     18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: 2'-OMe

<400> SEQUENCE: 51
ctatctagcg ttctctgt                                                     18

<210> SEQ ID NO 52
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 52
cctactagcg t                                                              11

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cctactagcg                                                                10

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 3'-deoxy-nucleoside-G

<400> SEQUENCE: 54
cctactancg ttctcatc                                                       18

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 3'-OMe-A

<400> SEQUENCE: 55
tccatgncgt tcctgatgc                                                      19

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: B-L-deoxy-nucleoside-C
<220> FEATURE:
<221> NAME/KEY: modified_base
<222> LOCATION: (10)
<223> OTHER INFORMATION: B-L-deoxy nucleoside-G

<400> SEQUENCE: 56
ctatctgann ttctctgt                                                       18

<210> SEQ ID NO 57
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: B-L-deoxy nucleoside-C
<220> FEATURE:
<221> NAME/KEY: modified_base
<222> LOCATION: (2)
<223> OTHER INFORMATION: B-L-deoxy nucleoside-T
<220> FEATURE:
<221> NAME/KEY: modified_base
<222> LOCATION: (3)
<223> OTHER INFORMATION: B-L-deoxy nucleoside-A
<220> FEATURE:
<221> NAME/KEY: modified_base
<222> LOCATION: (4)
<223> OTHER INFORMATION: B-L-deoxy nucleoside-T
<220> FEATURE:
<221> NAME/KEY: modified_base
<222> LOCATION: (5)
<223> OTHER INFORMATION: B-L-deoxy nucleoside-C
<220> FEATURE:
<221> NAME/KEY: modified_base
<222> LOCATION: (6)
<223> OTHER INFORMATION: B-L-deoxy nucleoside-T
<220> FEATURE:
<221> NAME/KEY: modified_base
<222> LOCATION: (7)
<223> OTHER INFORMATION: B-L-deoxy nucleoside-G
<220> FEATURE:
<221> NAME/KEY: modified_base
<222> LOCATION: (8)
<223> OTHER INFORMATION: B-L-deoxy nucleoside-A
<220> FEATURE:
<221> NAME/KEY: modified_base
<222> LOCATION: (9)
<223> OTHER INFORMATION: B-L-deoxy nucleoside-C
<220> FEATURE:
<221> NAME/KEY: modified_base
<222> LOCATION: (10)
<223> OTHER INFORMATION: B-L-deoxy nucleoside-G
<220> FEATURE:
<221> NAME/KEY: modified_base
<222> LOCATION: (11)
<223> OTHER INFORMATION: B-L-deoxy nucleoside-T
<220> FEATURE:
<221> NAME/KEY: modified_base
<222> LOCATION: (12)
<223> OTHER INFORMATION: B-L-deoxy nucleoside-T
<220> FEATURE:
<221> NAME/KEY: modified_base
<222> LOCATION: (13)
<223> OTHER INFORMATION: B-L-deoxy nucleoside-C
<220> FEATURE:
<221> NAME/KEY: modified_base
<222> LOCATION: (14)
<223> OTHER INFORMATION: B-L-deoxy nucleoside-T
<220> FEATURE:
<221> NAME/KEY: modified_base
<222> LOCATION: (15)
<223> OTHER INFORMATION: B-L-deoxy nucleoside-C
<220> FEATURE:
<221> NAME/KEY: modified_base
<222> LOCATION: (16)
<223> OTHER INFORMATION: B-L-deoxy nucleoside-T
<220> FEATURE:
<221> NAME/KEY: modified_base
<222> LOCATION: (17)
<223> OTHER INFORMATION: B-L-deoxy nucleoside-G
<220> FEATURE:
<221> NAME/KEY: modified_base
<222> LOCATION: (18)
<223> OTHER INFORMATION: B-L-deoxy nucleoside-T
```

```
<400> SEQUENCE: 57
nnnnnnnnnn nnnnnnnn                                              18

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctatctgacg t                                                     11

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctatctgacg                                                       10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctatctgacg                                                       10

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctatctagcg t                                                     11

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctatctagcg                                                       10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
```

-continued ctatctagcg                                                           10

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 64
ctatctaacg ttctctgt                                                  18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 65
ctatctagcg ttctctgt                                                  18

<210> SEQ ID NO 66
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 66
ctatctaucg ttctctgt                                                  18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 67
ctatctaacn ttctctgt                                                  18

```
<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 68
ctatctagcn ttctctgt                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 69
ctatctaucn ttctctgt                                                 18

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctatctagcg t                                                        11

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctatctagcg                                                          10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 72
ctatctagcg                                                                10

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tcctggaggg gaagt                                                          15

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 2'-OMe

<400> SEQUENCE: 74
ctatctgacg ttctctgt                                                       18

<210> SEQ ID NO 75
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (11)..(12)
<223> OTHER INFORMATION: 2'-OMe

<400> SEQUENCE: 75
ctatctgacn uuctctgt                                                       18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 3'-OMe-G

<400> SEQUENCE: 76
cctactancg ttctcatc                                                       18

<210> SEQ ID NO 77
<211> LENGTH: 19
<212> TYPE: DNA
```

<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-OMe-U

<400> SEQUENCE: 77
tccatgacgn tcctgatgc                                                    19

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgttctctgt                                                              10

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acgttctctg t                                                            11

<210> SEQ ID NO 80
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: dU

<400> SEQUENCE: 80
ctatctnacg ttctctgt                                                     18

<210> SEQ ID NO 81
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: dU

<400> SEQUENCE: 81

```
ctatctgncg ttctctgt                                              18
```

<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
ctatctgacg                                                       10
```

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
ctatctgacg t                                                     11
```

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

```
cgttctctgt                                                       10
```

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

```
acgttctctg t                                                     11
```

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe

<400> SEQUENCE: 86

```
tctgacgttc t                                                     11
```

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic

```
          oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 87
tctgacnttc t                                                        11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: araG

<400> SEQUENCE: 88
tctgacnttc t                                                        11

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(7)
<223> OTHER INFORMATION: 2'-OMe

<400> SEQUENCE: 89
tctctgacgt t                                                        11

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 90
tctgacnttc t                                                        11

<210> SEQ ID NO 91
<211> LENGTH: 18
<212> TYPE: DNA
<213> ORGANISM: Artificial Sequence
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: 2'-OMe

<400> SEQUENCE: 91
ctatctgtcg uuctctgt                                                    18

<210> SEQ ID NO 92
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (11)..(12)
<223> OTHER INFORMATION: 2'-OMe

<400> SEQUENCE: 92
ctatctgtcn uuctctgt                                                    18

<210> SEQ ID NO 93
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe

<400> SEQUENCE: 93
tctgucgttc t                                                           11

<210> SEQ ID NO 94
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 94
```
tctgucnttc t                                      11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: araG

<400> SEQUENCE: 95
tctgacnttc t                                      11

<210> SEQ ID NO 96
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 96 tctgacntt                                         9

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 97
tctgacnttc t                                      11

<210> SEQ ID NO 98
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 98
ctatctgacn ttctcugu                                                 18

<210> SEQ ID NO 99
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 99
ctatctgucn ttctcugu                                                 18

<210> SEQ ID NO 100
<211> LENGTH: 9
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)
<223> OTHER INFORMATION: 7-deaza-dG

<400> SEQUENCE: 100 ugucnttct                                                            9

<210> SEQ ID NO 101
<211> LENGTH: 9
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)
<223> OTHER INFORMATION: 7-deaza-dG

<400> SEQUENCE: 101 ugacnttct                                                                9
```